(12) United States Patent
Kawaura et al.

(10) Patent No.: US 8,911,464 B2
(45) Date of Patent: Dec. 16, 2014

(54) PUNCTURE APPARATUS

(71) Applicant: Terumo Kabushiki Kaisha, Shibuya-ku (JP)

(72) Inventors: Masakatsu Kawaura, Kanagawa (JP); Shigeki Ariura, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 92 days.

(21) Appl. No.: 13/840,940

(22) Filed: Mar. 15, 2013

(65) Prior Publication Data

US 2013/0253531 A1  Sep. 26, 2013

Related U.S. Application Data

(60) Provisional application No. 61/744,744, filed on Oct. 3, 2012.

(30) Foreign Application Priority Data

Mar. 23, 2012  (JP) ................ 2012-068400

(51) Int. Cl.

| A61B 17/34 | (2006.01) |
|---|---|
| A61B 17/42 | (2006.01) |
| A61B 17/04 | (2006.01) |
| A61B 17/062 | (2006.01) |
| A61B 17/06 | (2006.01) |
| A61B 17/00 | (2006.01) |

(52) U.S. Cl.
CPC .......... *A61B 17/3468* (2013.01); *A61B 17/42* (2013.01); *A61B 17/0482* (2013.01); *A61B 17/062* (2013.01); *A61B 17/06109* (2013.01); *A61B 2017/00805* (2013.01)
USPC ........................................ 606/185

(58) Field of Classification Search
USPC .............. 606/167, 170–172, 185; 600/29, 37
See application file for complete search history.

(56) References Cited

U.S. PATENT DOCUMENTS

| 6,911,003 B2 | 6/2005 | Anderson et al. |
|---|---|---|
| 7,131,943 B2 | 11/2006 | Kammerer |

FOREIGN PATENT DOCUMENTS

| WO | 93/19678 A2 | 10/1993 |
|---|---|---|
| WO | 98/35606 A2 | 8/1998 |
| WO | 2008/117307 A1 | 10/2008 |

OTHER PUBLICATIONS

International Search Report (Form PCT/ISA/210) issued on Sep. 3, 2013, by the European Patent Office in corresponding European International Application No. PCT/JP2013/001964. (2 pages).

*Primary Examiner* — Ryan Severson
(74) *Attorney, Agent, or Firm* — Buchanan Ingersoll & Rooney PC

(57) ABSTRACT

A puncture apparatus includes a puncture needle for puncturing living body tissue, an axial portion, a puncture member including an interlock portion interlocking the puncture needle and the axial portion, an elongated urethral-insertion member insertable into the urethra, an elongated vaginal-insertion member insertable into the vagina; and a supporting member supporting the puncture member, the urethral-insertion member and the vaginal-insertion member. The distal end of the puncture needle includes a sharp needle tip, and the needle is bent in an arc shape centered on the axial portion. The axial portion is freely rotatable on the supporting member, and the supporting member restricts the positional relation between the puncture member and the urethral-insertion member such that when the puncture member rotates and punctures the living body tissue, the needle tip passes a far-position side from the center of the puncture needle compared with the urethral-insertion member or an extended line of such member.

20 Claims, 21 Drawing Sheets

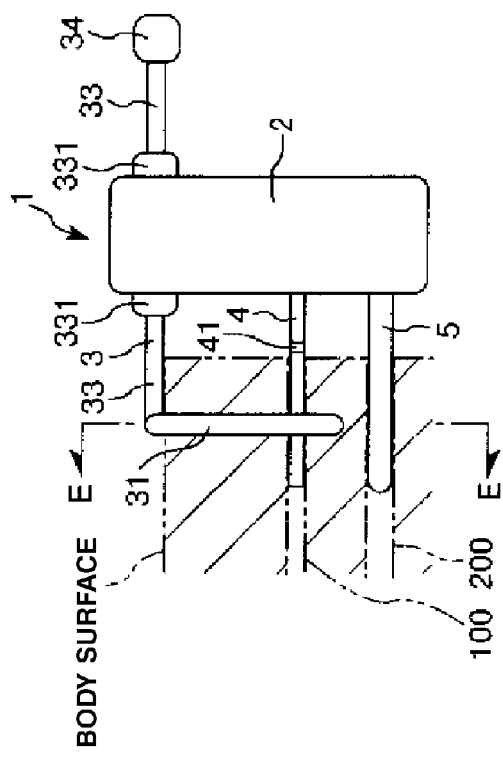
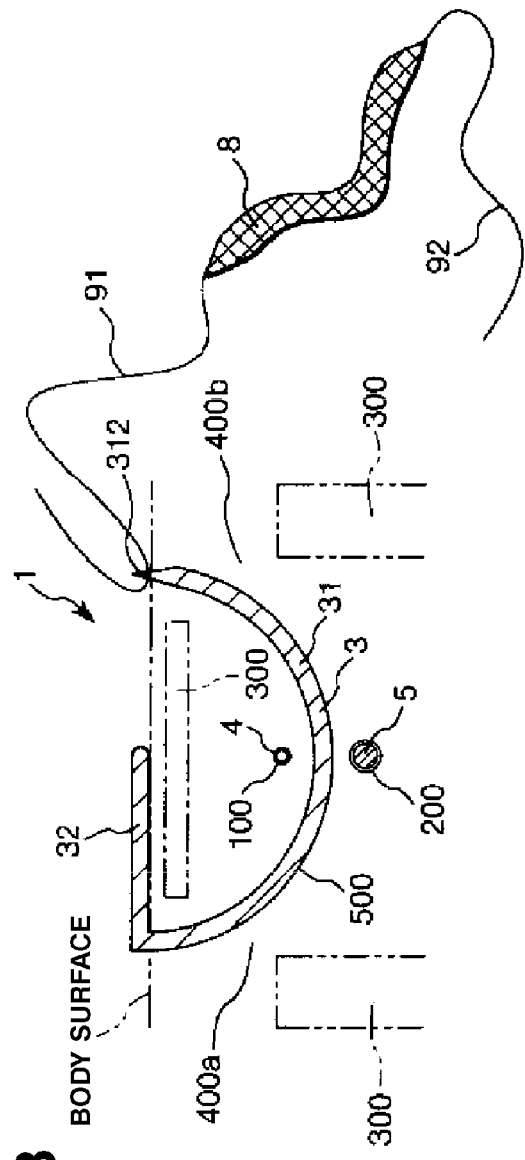
FIG. 7A
FIG. 7B

PUNCTURE APPARATUS

CROSS REFERENCES TO RELATED APPLICATIONS

This application contains subject matter disclosed in U.S. Application No. 61/744,744 filed on Oct. 3, 2012 and Japanese Patent Application No. 2012-068400 filed in the Japanese Patent Office on Mar. 23, 2012, the entire content of both of which is incorporated herein by reference.

TECHNOLOGICAL FIELD

The present invention generally relates to a puncture apparatus.

BACKGROUND DISCUSSION

When suffering from a urinary incontinence, in particular, when suffering from a stress urinary incontinence, urine leakage occurs caused by the fact that abdominal pressure is applied during a normal exercise or is applied by laughing, coughing, sneezing and the like. For this reason, it is possible to cite, for example, a fact that the pelvic floor muscle which is a muscle for supporting the urethra will loosen caused by a child-bearing or the like.

For the treatment of urinary incontinence, a surgical treatment is effective, in which there is used, for example, a tape-shaped implant referred to as "sling". The "sling" is implanted into the body and the urethra is supported by that sling. An example of this is disclosed in U.S. Pat. No. 6,911,003. In order to indwell the sling inside the body, an operator incises the vagina with a surgical knife, dissects a region between the urethra and the vagina, and communicates that exfoliated region and the outside through an obturator foramen by using a puncture needle or the like. Then, in such a state, the sling is implanted into the body.

However, if the vagina is once incised, there is a fear that there occurs a phenomenon in which the sling will be exposed to the inside of the vagina from a wound caused by the incision thereof, and there is a fear that complications may occur which are caused by an infection from the wound or the like. In addition, since the vagina is incised, the invasiveness of the procedure is rather great and the burden on the patient is large. In addition, there is a fear that the urethra or the like will be damaged in the course of the procedure by the operator, and also, there is a fear that the operator himself will damage his finger tip.

Also, like urinary incontinence, there exists a pelvic organ prolapse as another disorder from which a woman suffers. This disorder is a disorder in which a pelvic organ such as a uterus, a bladder or the like supported in a hammock shape by a pelvic floor muscle group is prolapsed from the vagina caused by the weakening of the pelvic floor muscle group, which can be caused by old age or the like and this is referred to also as a so-called hysterocele or as a cystocele or a rectocele. A repairing method for this pelvic organ prolapse has, in the past, involved a vaginal-wall shortening surgery (colporrhaphy) in which the vaginal wall was incised and the loosened tissue existing between the prolapsed organ and the vaginal wall is partially removed, sutured and shortened. But in recent years, as an alternative technology for that surgery, there has been employed a TVM (Tension-free Vaginal Mesh) surgery and it became possible to prevent the deviation of the pelvic organ from the vagina with lower invasion and also effectively by supporting the prolapsed organ in a hammock shape with a polypropylene-made mesh. An example of this alternative is described in U.S. Pat. No. 7,131,943.

However, like in the treatment of urinary incontinence, when the vagina is incised and the mesh is indwelled, there is a fear that there occurs a phenomenon in which the sling will be exposed to the inside of the vagina from a wound caused by the incision thereof, and there is a fear that there occur complications which are to be caused by an infection from the wound or the like. In addition, since the vagina is incised, the invasiveness of the procedure is rather significant, and the burden on the patient is large. In addition, there is a fear that the urethra or the like will be damaged in the course of the procedure by the operator, and also, there is a fear that the operator himself will damage his finger tip.

SUMMARY

According to one aspect, a puncture apparatus includes a freely rotatable puncture member possessing a distal end portion and a proximal end portion, wherein the puncture member includes a bent region at which the puncture member is bent, with the distal end portion of the puncture member including a puncture needle for puncturing living body tissue as the puncture member is rotated about a rotation center to rotate a needle tip of the puncture needle toward the living body tissue to puncture the living body tissue. The puncture apparatus also includes an elongated urethral-insertion member configured to be inserted into a urethra so that a near-side of the urethral-insertion member is the side of the urethral-insertion member located closer to the rotation center, and a far-side of the urethral-insertion member is the side of the urethral-insertion member located farther from the rotation center. The puncture apparatus also includes restriction means for restricting a positional relationship between the puncture member and the urethral-insertion member so that the needle tip of the puncture needle which is rotating about the rotation center after first puncturing the living body tissue passes on the far-side of the urethral-insertion member.

The puncture apparatus here is able to reduce the burden on the patient, while providing a high degree of safety to both the patient and the operator.

The puncture apparatus preferably also includes an elongated vaginal-insertion member which is insertable into a vagina, wherein the restriction means restricts the positional relation between the puncture member and the vaginal-insertion member such that the needle tip of the puncture needle will not interfere with the vaginal-insertion member when the puncture member moves rotationally and punctures the living body tissue.

It is preferable that the puncture member includes an axial portion which forms a rotational axis for the rotary movement, wherein the restriction means supports the axial portion in a freely rotatable manner, and concurrently includes a supporting member that supports the urethral-insertion member.

The puncture apparatus preferably also includes an elongated vaginal-insertion member, wherein the puncture member includes an axial portion forming a rotational axis for the rotary movement, and the restriction means restricts the positional relation between the puncture member and the vaginal-insertion member such that the needle tip of the puncture needle will not interfere with the vaginal-insertion member when the puncture member moves rotationally and punctures the living body tissue. The restriction means supports the axial portion in a freely rotatable manner, and concurrently includes a supporting member that supports the urethral-insertion member and the vaginal-insertion member respectively.

The puncture member is preferably freely detachable with respect to the supporting member. The axial portion can be supported by the supporting member movably in the axial direction of the urethral-insertion member.

In the puncture apparatus, the puncture member which is placed in a freely rotatable manner includes an axial portion connected to the puncture needle, and the axis line of the axial portion is inclined with respect to the axis line of the urethral-insertion member such that the distance of separation between the axis line of the axial portion and the axis line of the urethral-insertion member increases or decreases toward the distal side.

The puncture member can preferably include an operation unit for operating the puncture member rotationally. And the puncture needle can include a through-hole at the distal portion of the puncture needle. Also, the urethral insertion portion can be in a tubular shape. The puncture apparatus can also include a guide member for guiding the puncture needle.

According to another aspect, a puncture apparatus includes a freely rotatable puncture member, an elongated insertion member, and a restriction structure. The puncture member includes a bent region at which the puncture member is bent, and the distal end portion of the puncture member includes a puncture needle for puncturing living body tissue as the puncture member is rotated about a rotation center to rotate a needle tip of the puncture needle toward the living body tissue to puncture the living body tissue. The elongated insertion member is configured to be inserted inside a living body so that a near-side of the insertion member is the side of the insertion member located closer to the rotation center, and the far-side of the insertion member is the side of the insertion member located farther from the rotation center. The restriction structure is configured to restrict a positional relationship between the puncture member and the insertion member to position the needle tip of the puncture needle which is rotating about the rotation center after first puncturing the living body tissue on the far-side of the insertion member.

It is preferable for the insertion member to be a tubular-lumen insertion member which is insertable into a tubular lumen opened in the living body. And it is preferable for the insertion member to be a tissue-insertion member configured to be implanted into the tissue by being punctured from the surface of the living body. The insertion member can have a depth marker by which the insertion depth is visually recognizable or a marker which is visually recognizable under a noninvasive monitoring inside the body.

Another aspect of the disclosure here involves a method of forming a path for implanting an implant in order to treat a urinary incontinence. The method involves preparing a freely rotatable puncture member which includes a bent region and which includes a puncture needle for puncturing living body tissue, an elongated urethral-insertion member which is insertable into a urethra, and restriction means for restricting the positional relation between the puncture member and the urethral-insertion member such that the needle tip of the puncture needle will pass on the far-position side from the rotation center of the puncture needle relative to the urethral-insertion member when the puncture member rotates and punctures the living body tissue;

The urethral-insertion member is inserted into the urethra of a patient, and the puncture needle of the puncture member is made to puncture a body surface at one interlock region of the patient or at the region in the vicinity of such region, made to enter into the body, made to pass an obturator foramen of one pelvis, made to pass the far-position side of the urethra, made to pass an obturator foramen of the other pelvis and made to protrude to the outside of the body from the body surface of another interlock region or from the region in the vicinity of such region, whereby there is formed a through-hole reaching the another interlock region or the region in the vicinity thereof from the body surface at the one interlock region or at the region in the vicinity of such region by way of the obturator foramen of one pelvis, the far-position side of the urethra and the obturator foramen of the other pelvis.

According to another aspect, a method of forming a path in biological tissue of a living body comprises inserting an elongated insertion member of a puncture apparatus into a portion of a living body, wherein the puncture apparatus also includes a rotatable puncture member possessing a distal end portion at which is located a needle tip, rotating the puncture member in a rotational direction about a rotation center while the insertion member remains inserted in the living body to move the puncture member along a path of rotational movement, with the portion of the living body into which the insertion member is inserted being located relative to the rotation center of the path of rotational movement of the puncture member such that a near-side of the insertion member is the side of the insertion member located closer to the rotation center, and a far-side of the insertion member is the side of the insertion member located farther from the rotation center. The method additionally involves continuing to rotate the puncture member in the rotational direction about the rotation center while the insertion member remains inserted in the living body to cause the needle tip to puncture a surface of the living body tissue, and restricting a positional relationship of the puncture member and the insertion member while rotating the puncture member in the rotational direction to ensure that the path of rotational movement of the puncture member passes on the far-side of the insertion member.

Also disclosed is a method of forming a path for implanting an implant in order to treat a urinary incontinence, wherein there is prepared a freely rotatable puncture member which includes a bent region and a puncture needle for puncturing living body tissue, and when the puncture member is moved rotationally and the puncture needle of the puncture member punctures the living body tissue, the puncture needle is made to puncture a body surface at an interlock region of the patient or at the region in the vicinity of such region, is made to enter into the body and is made to pass an obturator foramen of a pelvis; and the puncture member is made to pass a far-position side from the rotation center of the puncture needle compared with the urethra, whereby the path is formed.

Another aspect involves a method of forming a path for implanting an implant in order to treat a urinary incontinence. The method includes preparing a puncture tool provided with a urethral-insertion member having a longitudinal shape, which is to be inserted into a urethra, and a puncture member which can puncture the living body tissue and which has such an orbit passing a far-position side compared with the urethral-insertion member; inserting the insertion member into a urethra of a patient; and wherein the puncture member is made to puncture into a body from the body surface at an interlock region of the patient or at the region in the vicinity of such region and made to pass an obturator foramen of a pelvis; and the puncture member is made to pass a far-position side compared with the urethral-insertion member, whereby the path is formed.

According to another aspect, a method of forming a path for implanting an implant in order to treat a pelvic floor disorder includes preparing a freely rotatable puncture member which includes a bent region and which includes a puncture needle for puncturing living body tissue, and when the puncture member is moved rotationally and the puncture needle of the puncture member punctures the living body tissue, the puncture needle is made to punctured a body surface of a patient and is made to enter into the body; and the puncture member is made to pass a far-position side from the rotation center of the puncture needle compared with the target region, whereby the path is formed.

Another aspect involves a method of forming a path for implanting an implant in order to treat a pelvic floor disorder, wherein a puncture tool is prepared to be provided with an insertion member having a longitudinal shape, which is to be inserted into a living body, and a puncture member which can puncture the living body tissue and which has such an orbit passing a far-position side compared with the insertion member; the insertion member is inserted into the body of a patient; and the puncture member is made to puncture into the body from the body surface of the patient; and the puncture member is made to pass a far-position side compared with the insertion member, whereby the path is formed.

BRIEF DESCRIPTION OF THE DRAWINGS

FIGS. 7A and 7B are views explaining an operating procedure of the puncture apparatus shown in FIG. 1, with FIG. 7B taken along the section line 7B-7B in FIG. 7A.

DETAILED DESCRIPTION

Figure 1:
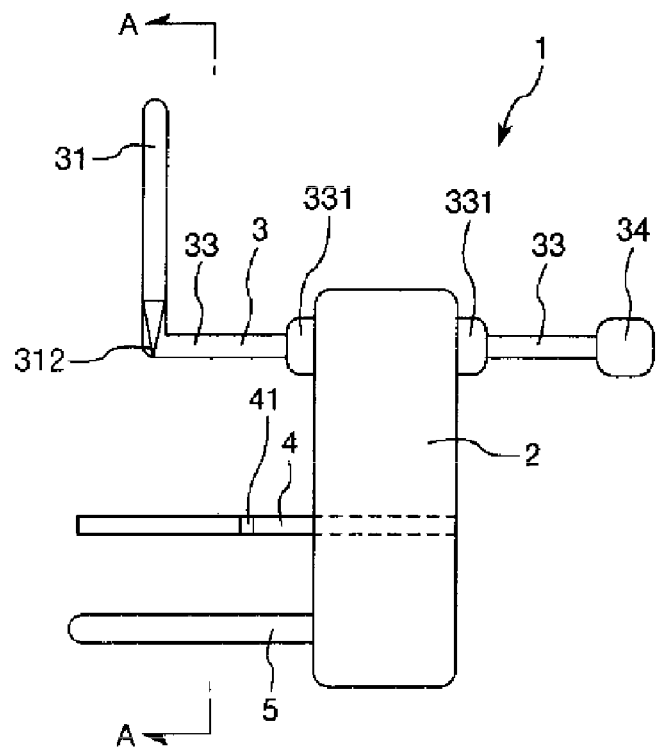
FIG. 1 is a side view of a first embodiment, disclosed by way of example, of a puncture apparatus disclosed here.

FIGS. 1-11 illustrate features and operational aspects of an embodiment of the puncture apparatus disclosed here. In FIG. 4B, FIG. 5B, FIG. 6B, FIG. 7B and FIGS. 8-11, the oblique lines for the living body are omitted so as to be more easily viewable. In the description which follows, the left side in FIG. 1, FIG. 3, FIG. 4A, FIG. 5A, FIG. 6A, FIG. 7A is the "distal end" and the right side is the "proximal end".

The puncture apparatus 1 shown in these drawings is an apparatus to be used for the treatment of woman's urinary incontinence. That is, it is to be used when burying an implant (tool implanted into a living body) for the treatment of urinary incontinence inside the living body.

The implant is a buriable tool for the treatment of woman's urinary incontinence, that is, a tool for supporting the urethra and a tool for supporting the urethra thereof so as to pull it to the direction separated from the vaginal wall when, for example, the urethra is going to move to the vaginal-wall side. For this implant, it is possible to use, for example, a long object having flexibility.

As shown in FIG. 7B, in this embodiment disclosed by way of example, an implant 8 forms an elongated bogy having a mesh-like shape (mesh-shaped) and the overall shape of the implant is a belt-like shape. This implant 8 is referred to as a "sling". It is possible for the implant 8 to be configured as an implant braided in a mesh-like shape (lattice shape), for example, by intersecting line shaped bodies, that is, to be constituted by a braided body having a mesh-like shape. For the line shaped body, examples include a body whose cross-sectional shape is a round shape; whose cross-sectional shape is a flattened shaped, that is, a belt-like shape (ribbon shape); or the like. In addition, at the one end portion of the implant 8, one end portion of a string 91 is fixed and at the other end portion thereof, one end portion of a string 92 is fixed.

Also, there is no limitation in particular for the material forming the implant 8, and it is possible to use, for example, various kinds of resin materials and the like which are biocompatible Also, there is no limitation in particular for the materials forming the strings 91, 92, and it is possible to use, for example, various kinds of resin materials, fibers and the like.

The shape of the implant 8 is not limited to the above-described mesh-like shape.

Figure 2:
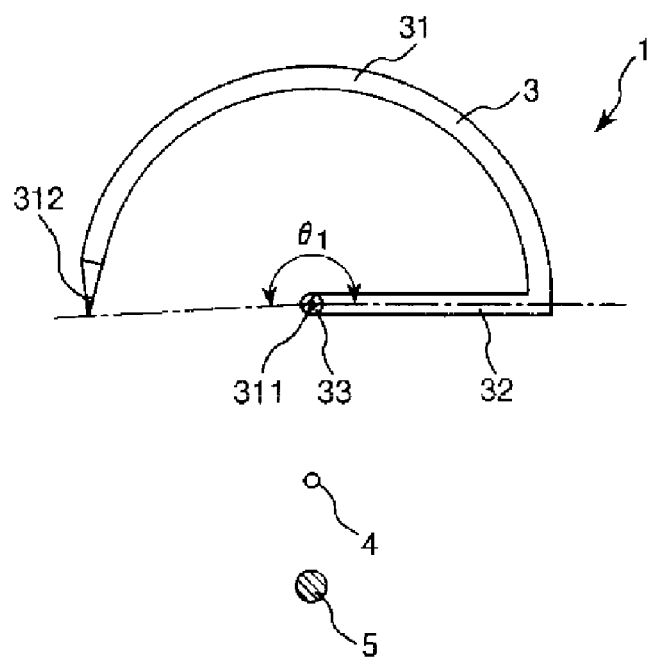
FIG. 2 is a cross-sectional view along the section line 2-2 in FIG. 1.

As shown in FIG. 1 and FIG. 2, the puncture apparatus 1 includes a puncture member 3, a urethral-insertion member 4 possessing an elongated shape and sized and configured to be inserted into a urethra, a vaginal-insertion member 5 possessing an elongated shape and sized and configured to be inserted into a vagina; and a supporting member 2 for supporting the puncture member 3, the urethral-insertion member 4 and the vaginal-insertion member 5. The supporting member 2 is an example of a restriction means for restricting the positional relationship between the puncture member 3 and the urethral-insertion member 4 (and also the vaginal-insertion member 5, if desired), as will be discussed in more detail below. The puncture member 3 includes a puncture needle 31 at a distal end portion of the puncture member for puncturing living body tissue, an axial portion 33 and an interlock portion 32 connecting the puncture needle 31 and the axial portion 33.

Figure 3:
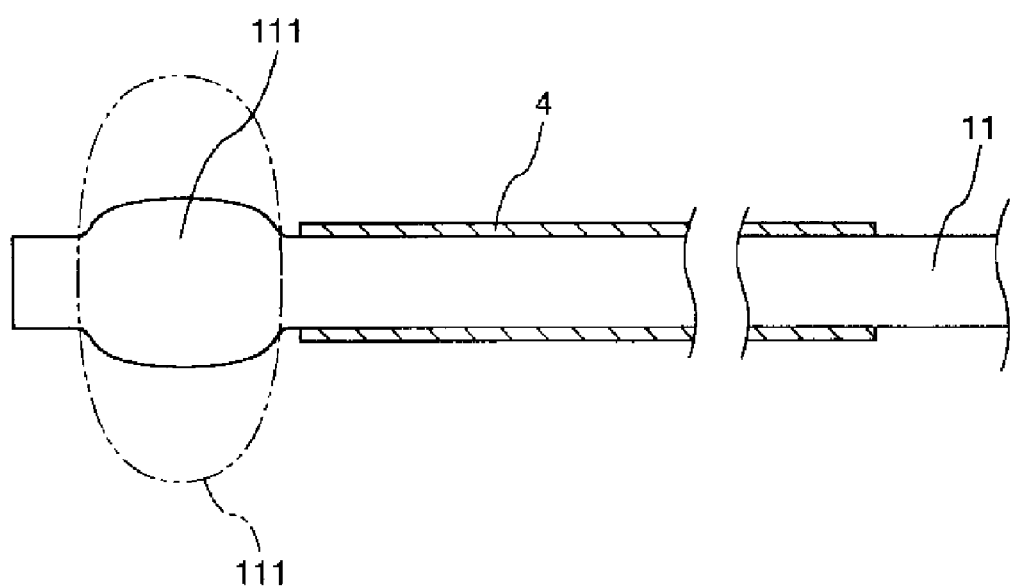
FIG. 3 is a cross-sectional view showing a state in which a balloon catheter is inserted into a urethral-insertion member of the puncture apparatus shown in FIG. 1.

In this embodiment, the urethral-insertion member 4 is firmly-fixed to the supporting member 2. This urethral-insertion member 4 is a straight tubular-shaped body composed of a non-elastic rigid material, and has an opening at the proximal end that opens to the proximal surface of the supporting member 2. It is possible to insert into the inside of the urethral-insertion member 4 various kinds of long-shaped (elongated) medical tools such as, for example, a balloon catheter 11, which is provided with an expandable and contractible balloon 111 at its distal portion such as shown in FIG. 3. In FIG. 3, a state in which the balloon 111 is contracted is indicated by a solid line and a state in which the balloon 111 is expanded is indicated by a two-dot chain line.

The balloon 111 of this balloon catheter 11 functions as a restriction structure for restricting the position of the urethral-insertion member 4 in the axis direction (longitudinal direction) inside the urethra. More specifically, when using the puncture apparatus 1, the balloon 111 is inserted into a bladder of a patient, the positional relation in the axial direction between the balloon catheter 11 and the urethral-insertion member 4 is fixed, and also, by a mechanism in which the balloon 111 is hooked onto the bladder neck in a state of being expanded, the position of the urethral-insertion member 4 with respect to the bladder and the urethra is fixed.

A balloon expanding tool such as, for example, a syringe is connected to a port which communicates with a lumen in communication with the balloon 111 of the balloon catheter 11. The expansion and contraction of the balloon 111 is carried out by feeding an operating fluid supplied by that balloon expanding tool into the inside of the balloon 111 through the mentioned lumen or by pulling out the operating fluid. As the operating fluid for the expansion of the balloon, it is possible to use, for example, a liquid such as a physiological saline or the like, a gas, and the like.

Also, it is possible to use the balloon catheter 11 for the urination of the patient when using the puncture apparatus 1.

A marker 41 is also provided at the outer circumferential portion of the urethral-insertion member 4. This marker 41 is arranged such that the marker 41 is positioned at the urethral opening when the urethral-insertion member 4 is inserted into the urethra and the distal portion of the urethral-insertion member 4 is positioned just before the bladder.

In this embodiment, the vaginal-insertion member 5 is firmly-fixed to the supporting member 2. This vaginal-insertion member 5 is a straight bar shape. Also, the distal portion of the vaginal-insertion member 5 is rounded. Thus, it is possible to insert the vaginal-insertion member 5 smoothly into the vagina.

Also, the vaginal-insertion member 5 is arranged on the lower side of the urethral-insertion member 4 and is separated or spaced from the urethral-insertion member 4 by a predetermined distance such that the axis of the vaginal-insertion member 5 and the axis of the urethral-insertion member 4 are parallel. Preferably at least a proximal portion of the vaginal-insertion member 5 may be parallel with a proximal portion of the urethral-insertion member 4.

There is no limitation in particular for the materials forming the vaginal-insertion member 5, the urethral-insertion member 4 and the supporting member 2. It is possible to use, for example, various kinds of resin materials or the like, or various kind of metal materials or the like.

With regard to the puncture member 3, the axial portion 33 of the puncture member, also constituting the rotational axis of the puncture member, is placed (mounted) in a freely rotatable manner on the supporting member 2.

Also, the axial portion 33 is arranged on the upper side of the urethral-insertion member 4 and is separated or spaced from the urethral-insertion member 4 by a predetermined distance such that the axis of the axial portion 33 and the axis of the urethral-insertion member 4 are parallel. Also, when seen from the axial direction of the axial portion 33, the axial portion 33, the urethral-insertion member 4 and the vaginal-insertion member 5 are arranged on a straight line. The axis of the axial portion 33 exists in the same plane (plane surface) as that of the axis of the urethral-insertion member 4. The axis of the axial portion 33 also exists on the same plane (plane surface) same as that of the axis of the vaginal insertion member 5. Thus, as seen in FIG. 2, the axis of the axial portion 33, the axis of the urethral-insertion member 4, and the axis of the vaginal insertion member 5 lie in a common plane (a plane perpendicular to the plane of the paper).

This axial portion 33 passes completely through the supporting member 2 in the right and left direction in FIG. 1. On the distal side and the proximal side of the axial portion 33, there are formed a flange 331 and a flange 332 respectively through the supporting member 2, and depending on these flanges 331, 332, the movement toward the axis direction of the axial portion 33 with respect to the supporting member 2 is blocked.

The distal end of the puncture needle 31 has a sharp needle tip, and the puncture needle 31 bends in an arc shape centered on the axial portion 33. Also, in FIG. 1, the axis of the puncture needle 31 and the axis of the axial portion 33 are orthogonal. Thus, when the puncture member 3 is moved rotationally, the needle tip of the puncture needle 31 moves along the arc in a surface perpendicular to the axis of the axial portion 33 and more specifically, moves in a surface in which the aforesaid axis is a normal line.

The puncture needle 31 moves along a predetermined orbit. It is possible for the needle tip of the puncture needle 31 to move by drawing a preliminarily defined arc-shaped orbit centered on the axial portion 33. The orbit of the puncture needle 31 passes a far-position side compared with the urethral-insertion member 4. The orbit of the puncture needle 31 passes a portion between the urethral-insertion member 4 and vaginal-insertion member 5.

There is no problem even if the distal end of the puncture needle 31 has an obtuse needle tip of such a degree in which there is no obstacle to progress toward the inside of the living body tissue. It is possible to employ another or different member for the needle tip of the puncture needle 31.

Also, in this embodiment disclosed by way of example, the needle tip of the puncture needle 31 is directed toward the counterclockwise direction in FIG. 2, but it is not limited to this configuration as it is also possible for the needle to be directed toward the clockwise direction in FIG. 2.

It is also possible for the puncture needle 31 to be solid and it is also possible for the needle to have a tubular and hollow shape.

Also, in this embodiment, the puncture needle 31 is arranged on the proximal side relative to the distal portion (distal-most end) of the urethral-insertion member 4 in the axial direction of the urethral-insertion member 4.

It is also possible however for the puncture needle 31 to be arranged at the same position as the distal portion (distal-most end) of the urethral-insertion member 4 in the axial direction of the urethral-insertion member 4. Additionally, the needle 32 can be arranged on the distal side of the distal portion (distal-most end) of the urethral-insertion member 4.

Here, the supporting member 2 restricts the positional relation between the puncture member 3 and the urethral-insertion member 4 such that when the puncture member 3 moves rotationally (rotates) and punctures the living body tissue, the needle tip of the puncture needle 31 passes, relative to the urethral-insertion member 4 or an extended line (imaginary continuation) of such member, a far-position side from the center 311 of the puncture needle 31 so that is passes to a lower side of the urethral-insertion member 4 or an extended line of such member. That is, during rotation of the needle 31, the tip of the needle passes on the side (lower side in FIG. 2) of the urethral-insertion member 4 that is opposite the rotation center 33 of the needle such that the urethral-insertion member 4 is positioned between the center 33 and the lower portion of the path of movement of the needle tip. The center 311 of the puncture needle 31 is the center of the arc in the puncture needle 31, that is, is the rotary center of the puncture needle 31 (puncture member 3).

The positional relationship between the puncture member 3 and the urethral-insertion member 4 is fixed such that the orbit of the needle tip of the puncture member 3 does not intersect the urethral-insertion member 4 or the extended line thereof and such that the orbit of the needle tip of the puncture needle 31 will pass the lower side of the urethral-insertion member 4 or the extended line (imaginary extension) of such line.

With regard to the positional relation between the orbit of the needle tip of the puncture member 3 and the urethral-insertion member 4, other than the configuration in which the position is maintain by such a member as the aforementioned supporting member 2, it is possible to employ a guide member which is connected with the urethral-insertion member 4 and which is insertable into the urethral-insertion member 4 such that the puncture member 3 makes a movement by a certain orbit. Also, it is possible to employ a configuration in which the urethral-insertion member 4 and the puncture member 3 are connected directly and the puncture member 3 is configured to make a movement by a certain orbit, whereby the positional relation is fixed such that the orbit of the needle tip of the puncture needle 31 will pass the lower side of the urethral-insertion member 4 or the extended line thereof.

Also, it is possible for the urethral-insertion member 4 to be provided with a marker which is visually recognizable under the noninvasive monitoring of the inside of the body by X-ray, ultrasound or the like. While confirming the position of the urethral-insertion member 4 by a monitor while emitting the X-ray or the ultrasound, it is possible to pass the needle tip through a desired position by setting a condition in which the orbit of the needle tip of the puncture needle 31 will surely pass the lower side of the urethra and by executing the puncture. Further, it is possible for the vaginal insertion member 5 to be provided with a similar marker. It is possible to employ a configuration in which the orbit of the needle tip of the puncture needle 31 is displayed on the monitor such that the position of the urethral-insertion member 4 and the position of the orbit can be confirmed on the monitor. In a case in which the position of the urethral-insertion member 4 and the position of the orbit on the monitor intersect each other, a mechanism can be provided which can move the puncture member 3 automatically or manually such that the position of the orbit does not overlap. When employing such an embodiment, the positional relation between the orbit of the needle tip of the puncture needle 31 and the urethral-insertion member 4 can be maintained by a series of systems including the mechanism mentioned above.

Further, the supporting member 2 restricts the positional relation between the puncture member 3 and the vaginal-insertion member 5 such that when the puncture member 3 moves rotationally and punctures the living body tissue, the needle tip of the puncture needle 31 does not interfere with the vaginal-insertion member 5 and the extended line thereof.

More specifically, the supporting member 2 restricts the positional relation between the puncture member 3, the urethral-insertion member 4 and the vaginal-insertion member 5 such that when the puncture member 3 rotates or moves rotationally and punctures the living body tissue, the needle tip of the puncture needle 31 passes a position between the urethral-insertion member 4 or the extended line thereof and the vaginal-insertion member 5 or the extended line thereof.

Thus, depending on the puncture needle 31, it is possible to puncture the living body tissue by avoiding the urethra and the vaginal wall, and it is possible to prevent a phenomenon in which the puncture needle 31 will puncture the urethra and will puncture the vaginal wall.

Also, the orbit of the needle tip of the puncture needle 31 is determined so that it is possible for the operator himself to prevent a phenomenon of puncturing his finger tip by the puncture needle 31. Safety can thus be obtained.

There is no limitation in particular for the center angle θ1 of the arc of the puncture needle 31. This angle is an angle to be set arbitrarily in response to various conditions, and this angle is set such that when puncturing living body tissue by the puncture needle 31, it becomes possible for the puncture needle 31 to enter into the body from one body surface of the patient, to pass the lower side of the urethra and to protrude to the body outside from the other body surface.

Specifically, it is preferable for the center angle θ1 of the arc of the puncture needle 31 to be 150° to 270°, more preferably 170° to 250° or less, and still more preferably 190° to 230°.

Thus, when puncturing living body tissue by the puncture needle 31, it is possible for the puncture needle 31 to reliably enter into the body from one body surface of the patient, to pass the lower side of the urethra and to protrude to the body outside from the other body surface.

Also, at the distal portion of the puncture needle 31, there is formed a through-hole 312. This through-hole 312 passes through the puncture needle 31 toward the direction which is perpendicular with respect to the axis of the puncture needle 31. Also, either one of the strings 91, 92 which are fixed to the aforementioned implant 8 is inserted into this through-hole 312 and is detachably held (see FIG. 7B).

Also, at the proximal portion of the axial portion 33, there is provided a grasping unit 34 as an operation unit for operating the puncture member 3 rotationally. In this embodiment disclosed by way of example, this grasping unit 34 is in the shape of a rectangular solid. When moving the puncture member 3 rotationally, the grasping unit 34 is grasped by hand and fingers, and is moved rotationally toward a predetermined direction. Needless to say, the shape of the grasping unit 34 is not limited by the illustrated and described configuration.

There is no limitation in particular for the material forming the puncture member 3 and it is possible to use various kinds of rigid materials, such as metal materials, such as metal materials and resin materials. Examples of metal materials include stainless steel, aluminum or aluminum alloy and titanium or titanium alloy, or the like, and examples of resin materials include polyimide or polyamide, or the like. Puncture member 3 may include an outer elongate tube and an inner solid shaft.

Set forth next is a description of an operating procedure using the puncture apparatus 1, that is, a procedure when burying the implant 8 inside the living body.

Initially, there will be explained a method of forming a path for burying the implant 8 inside the living body.

Figure 4A:
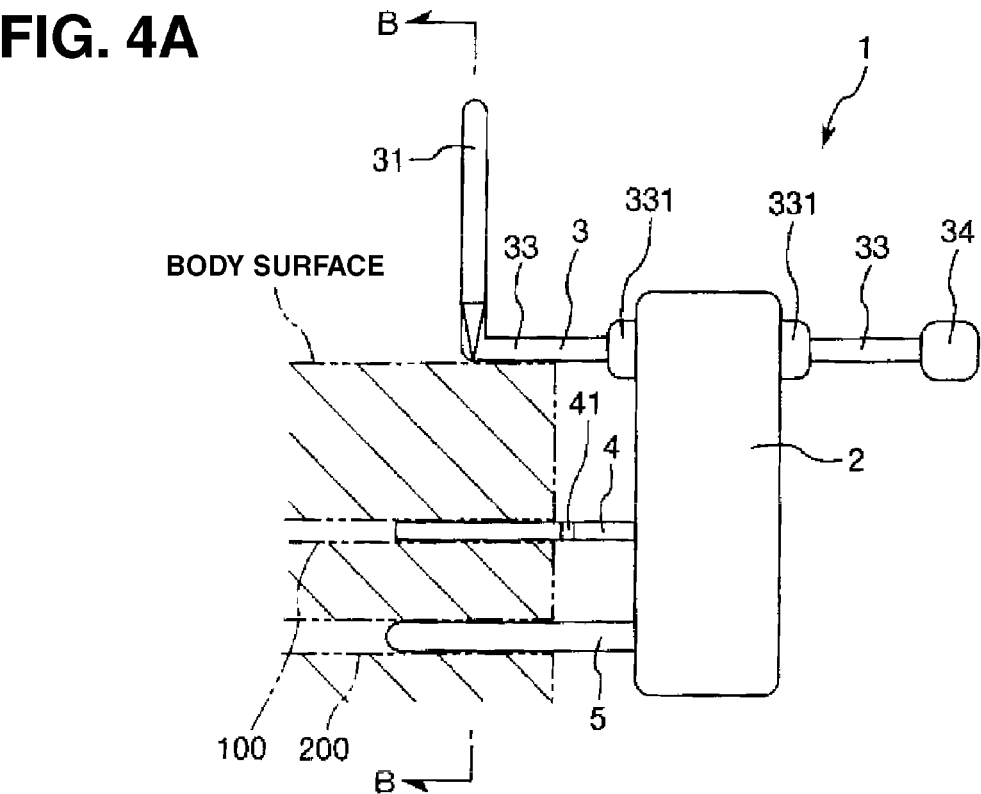
FIGS. 4A and 4B are views explaining an operating procedure of the puncture apparatus shown in FIG. 1, with FIG. 4B taken along the section line 4B-4B in FIG. 4A.
Figure 4B:
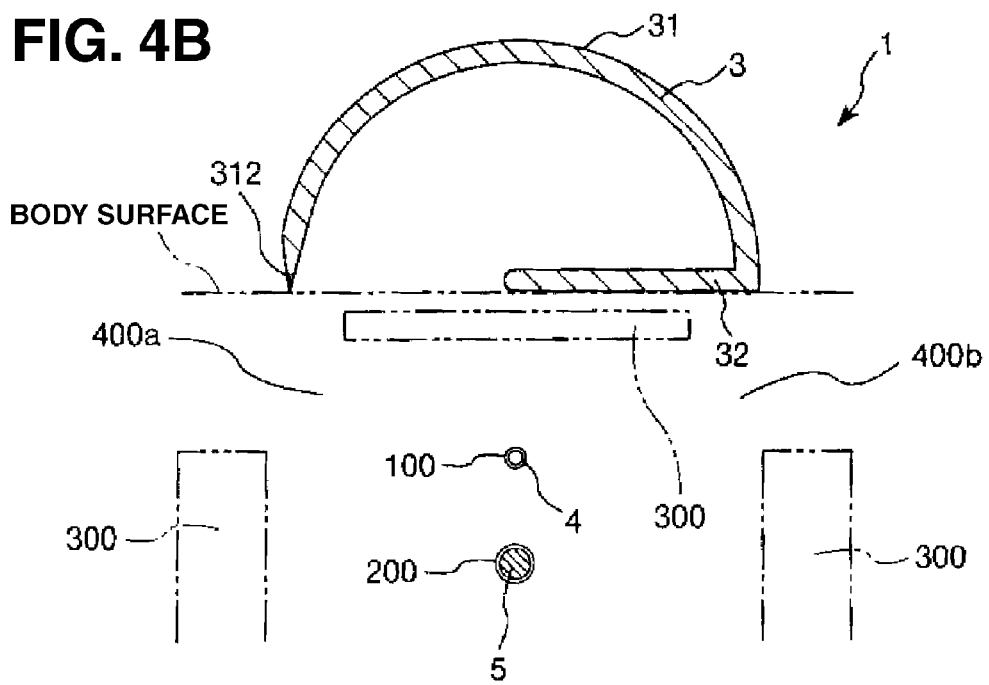

First, as shown in FIGS. 4A and 4B, the puncture apparatus 1 is attached to a patient. More specifically, the urethral-insertion member 4 of the puncture apparatus 1 is inserted into a urethra 100 of the patient and concurrently, the vaginal-insertion member 5 is inserted into a vagina 200 of the patient. At that time, the insertion is carried out such that the marker 41 will be positioned at the urethral orifice or on the front side of the urethral orifice. Thus, it is possible to arrange the distal portion of the urethral-insertion member 4 on the front side of the bladder.

Figure 5A:
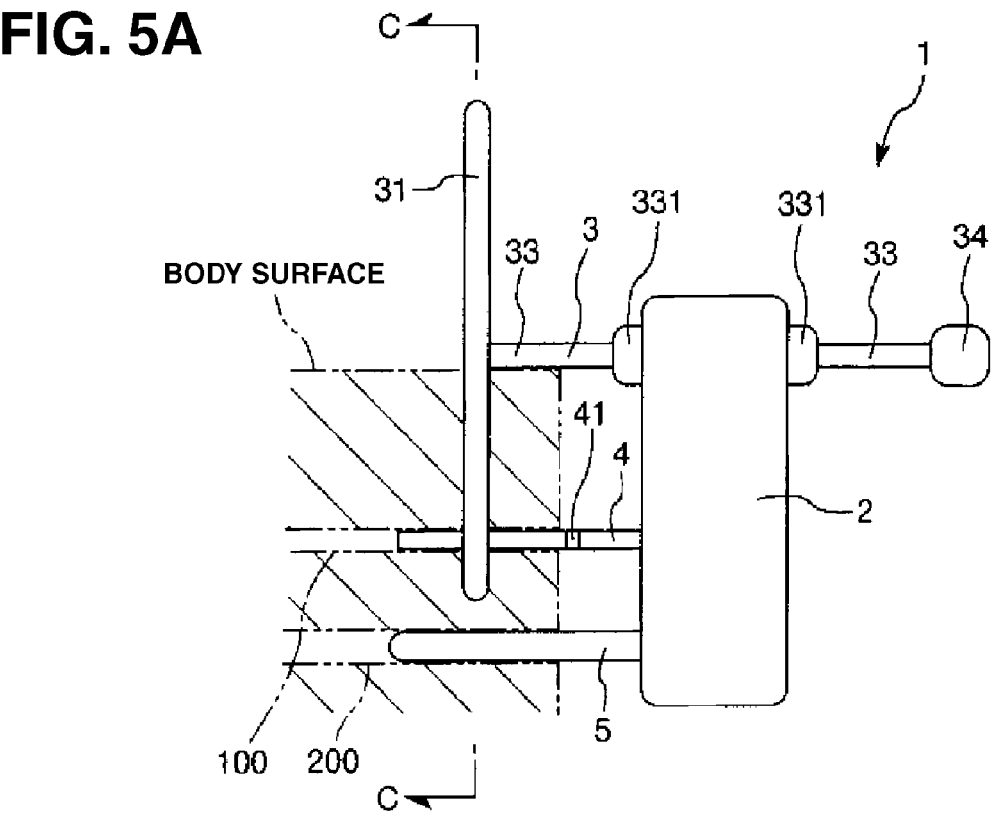
FIGS. 5A and 5B are views explaining an operating procedure of the puncture apparatus shown in FIG. 1, with FIG. 5B taken along the section line 5B-5B in FIG. 5A.
Figure 5B:
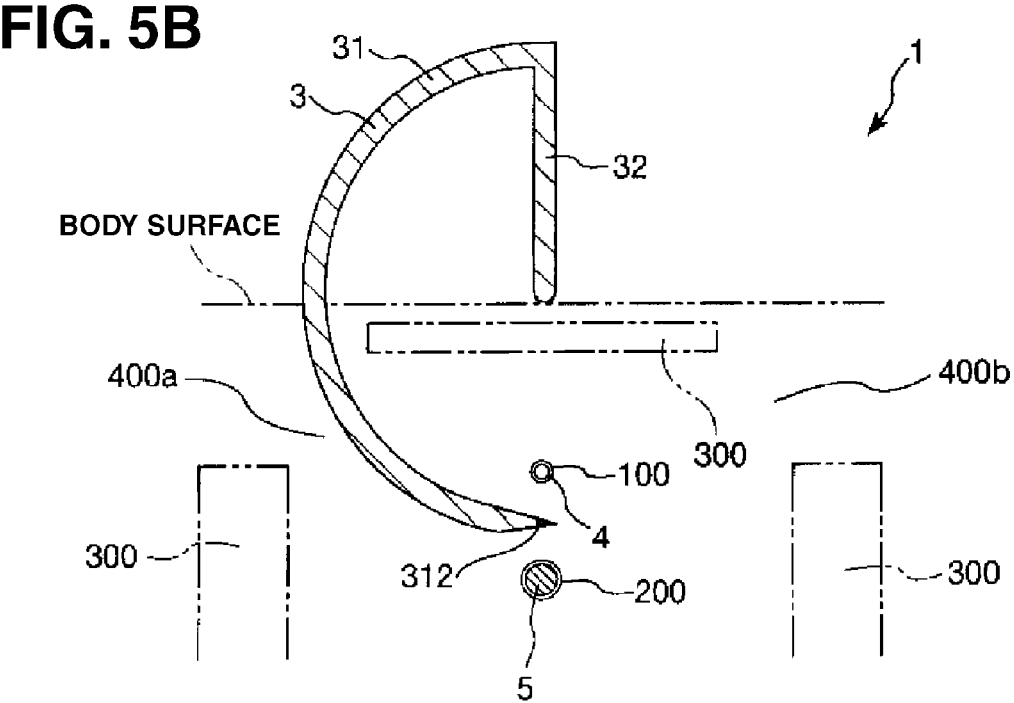
Figure 6A:
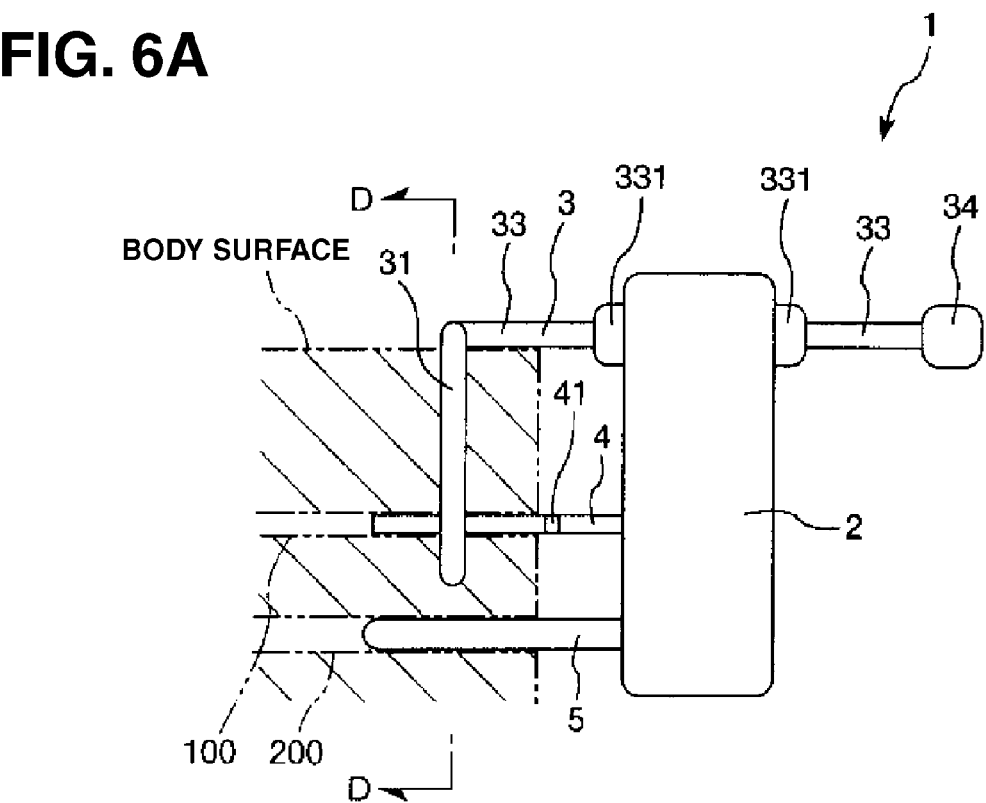
FIGS. 6A and 6B are views explaining an operating procedure of the puncture apparatus shown in FIG. 1, with FIG. 6B taken along the section line 6B-6B in FIG. 6A.
Figure 6B:
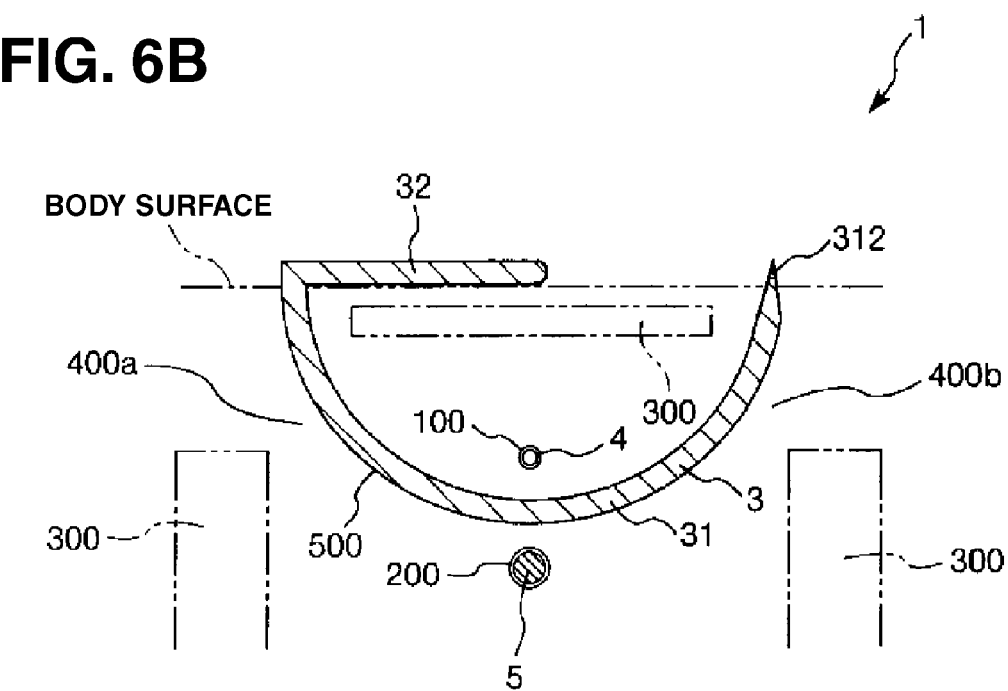

Next, as shown in FIGS. 5A, 5B, 6A and 6B, the grasping unit 34 is grasped and the puncture member 3 is rotated counterclockwise in FIG. 5B and FIG. 6B.

Thus, the member 3 percutaneously moves into a tissue of the body. First the needle tip of the puncture needle 31 moves counterclockwise in FIG. 5B and FIG. 6B along the arc of the needle; punctures the body surface at an interlock region of the patient on the left side in FIG. 5B and FIG. 6B or at a region in the vicinity of such region; enters into the body; passes an obturator foramen 400a of a pelvis 300; passes the lower side of the urethra 100, that is, passes between the urethra 100 and the vagina 200; passes an obturator foramen 400b of the pelvis 300; and protrudes back outside the body be exiting the body surface at an interlock region on the right side in FIG. 5B and FIG. 6B or at a region in the vicinity of such region. Thus, for the patient, there is formed a through-hole 500 which starts from the body surface at an interlock region on the left side in FIG. 5B and FIG. 6B or at a region in the vicinity of such region and which reaches the body surface at an interlock region on the right side in FIG. 5B and FIG. 6B or at a region in the vicinity of such region by passing through the obturator foramen 400a, the space between the urethra 100 and the vagina 200 and the obturator foramen 400b.

The through-hole 500 maintains a non-opened state with respect to the urethra 100 and the vagina 200. It is preferable for the orbit of the needle tip of the puncture needle 31 to pass a region on the inner side (near the pubic-bone connection) from the center of the obturator foramen 400b of the pelvis 300. It is more preferable for the orbit to pass a region referred to as a so-called safety zone (or safety-entry zone) within the regions near the pubic-bone connection from the center of the obturator foramen 400b. This is because there are few nerves or blood vessels in such regions, for which injuries are desired to be avoided, and because it is possible to carry out the puncture safely.

There will next be explained a procedure of passing an implant through the path and indwelling the implant.

As shown in FIGS. 7A and 7B, the end portion of either one of the strings 91, 92 fixed to the implant 8 is inserted through the through-hole 312 of the puncture needle 31, there is inserted the end portion of either one of the strings 91, 92 fixed to the implant 8. In the illustrated example, the end portion of string 91 is inserted through the through-hole 312 of the puncture needle 31. Thus, the end portion of the string 91 is held at the distal portion of the puncture needle 31.

Figure 8:
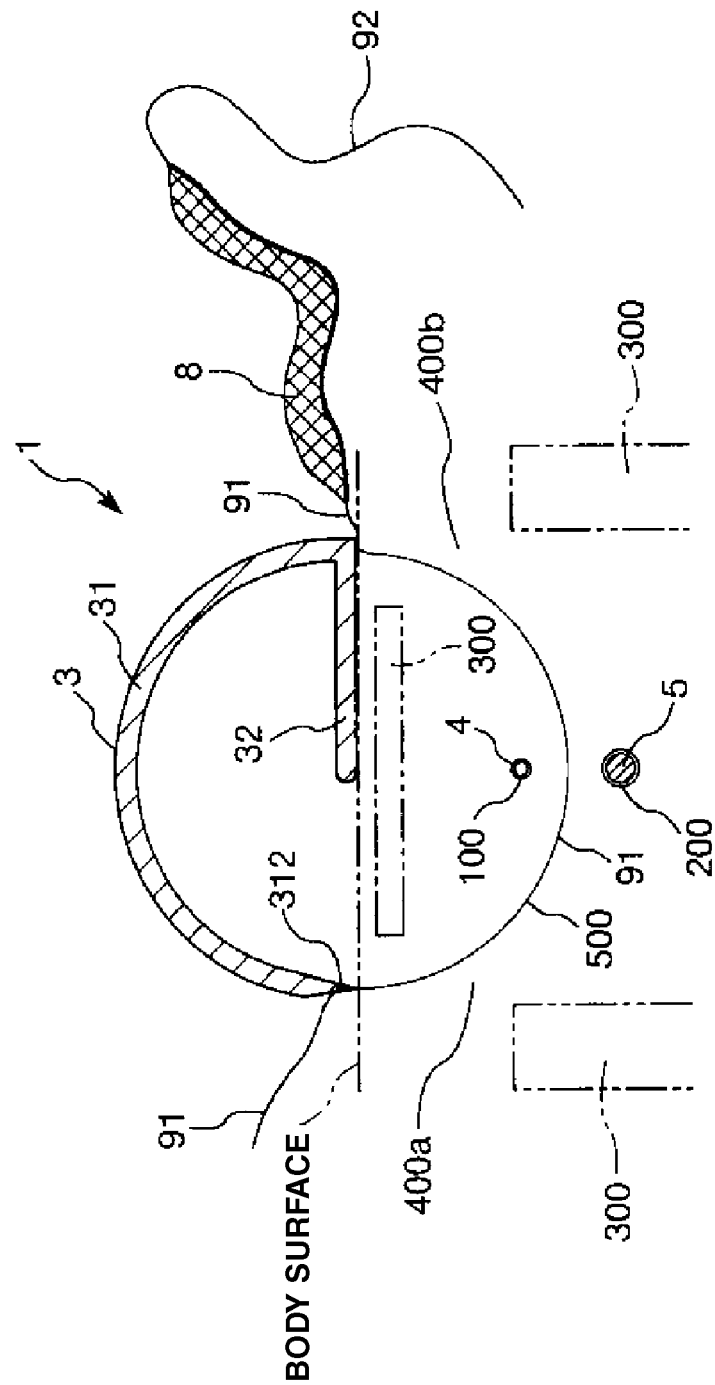
FIG. 8 is a cross-sectional view explaining an operating procedure of the puncture apparatus shown in FIG. 1.

Next, as shown in FIG. 8, the grasping unit 34 is grasped and the puncture member 3 is rotated clockwise in FIG. 8.

Thus, the needle tip of the puncture needle 31 moves clockwise in FIG. 8 along an arc; enters the body from the interlock region of the patient on the right side in FIG. 8 or from a body surface in a region in the vicinity of such region; passes the obturator foramen 400b of the pelvis 300; passes the lower side of the urethra 100, that is, passes between the urethra 100 and the vagina 200; passes the obturator foramen 400a of the pelvis 300; and exits to the outside of the body from the interlock region on the left side in FIG. 8 or from a body surface in a region in the vicinity of such region. More specifically, the puncture needle 31 is pulled out or moved to the outside of the body.

Figure 9:
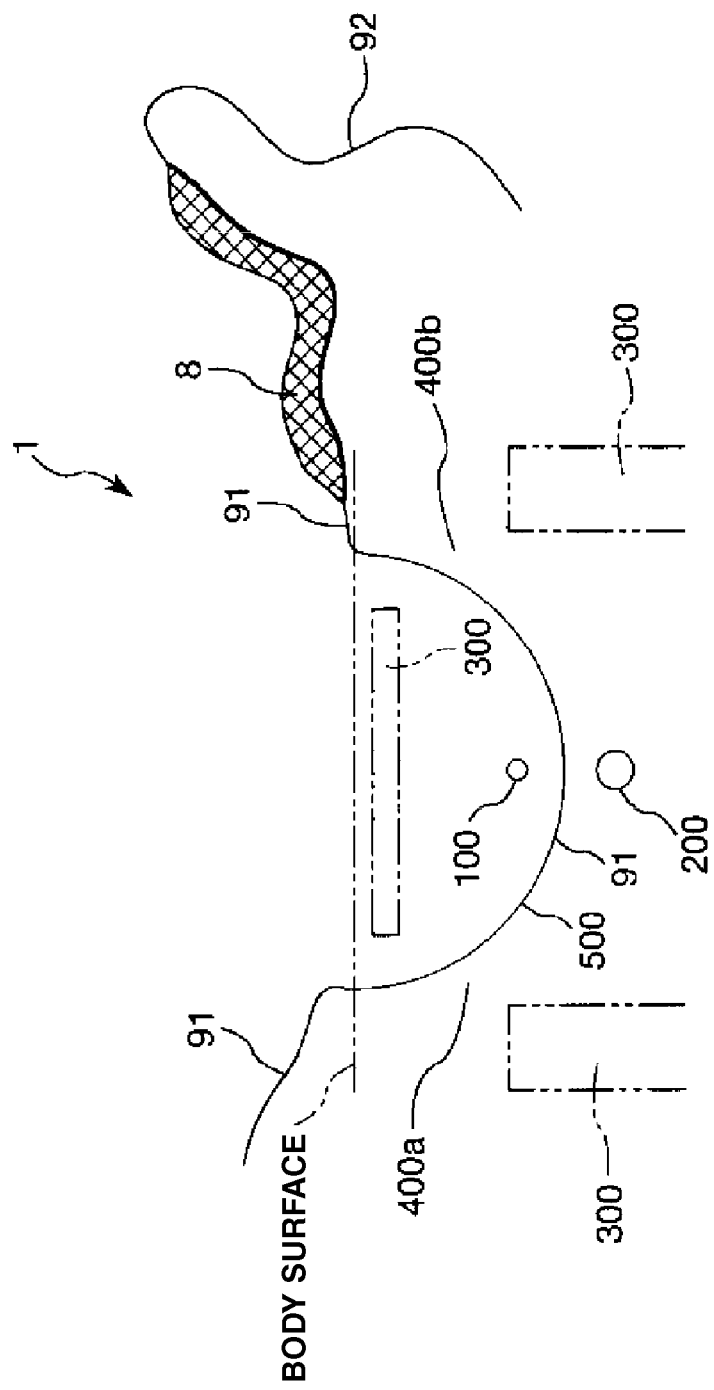
FIG. 9 is a cross-sectional view explaining an operating procedure of the puncture apparatus shown in FIG. 1.

Next, as shown in FIG. 9, the end portion of the string 91 is pulled out from the through-hole 312 of the puncture needle 31. Also, the puncture apparatus 1 is removed from the patient. More specifically, the urethral-insertion member 4 is pulled out from the inside of the urethra 100 and concurrently, the vaginal-insertion member 5 is pulled out from the inside of the vagina 200 of the patient.

Figure 10:
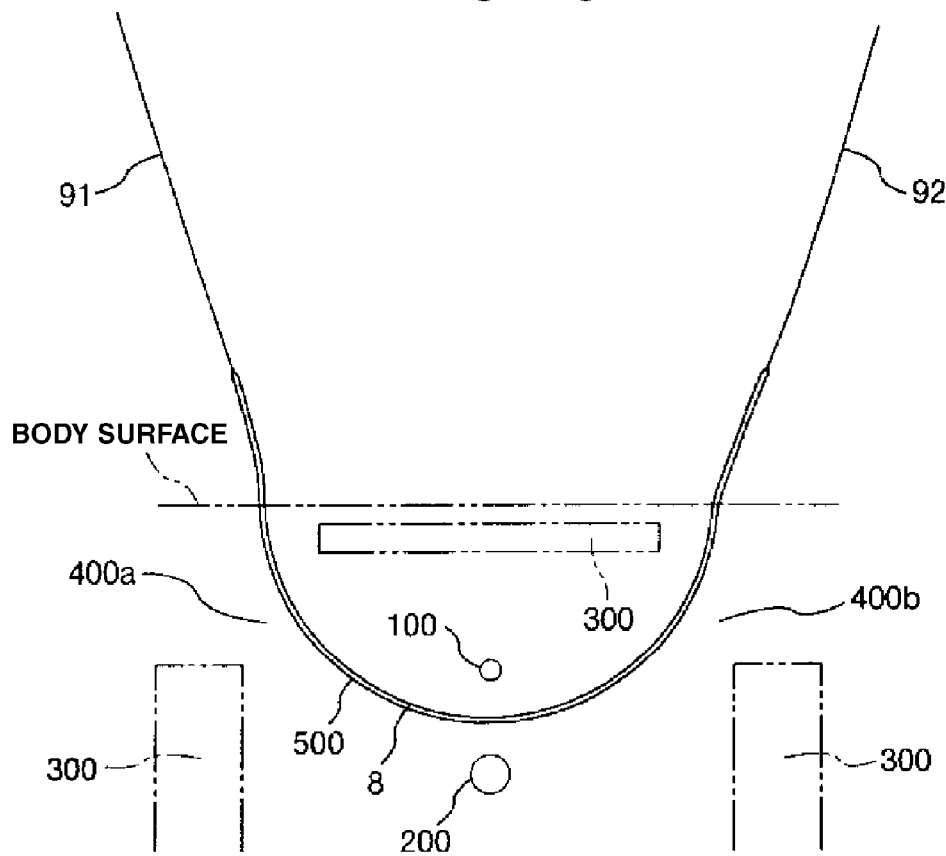
FIG. 10 is a cross-sectional view explaining an operating procedure of the puncture apparatus shown in FIG. 1.

Next, as shown in FIG. 10, the string 91 is pulled while pulling the string 92, the implant 8 is inserted into the through-hole 500 which is formed in the patient; and while the end portion of the implant 8 on the right side in FIG. 10 is remained on the outside of the body, the end portion of the implant 8 on the left side in FIG. 10 is pulled out from the through-hole 500 to the outside of the body.

Figure 11:
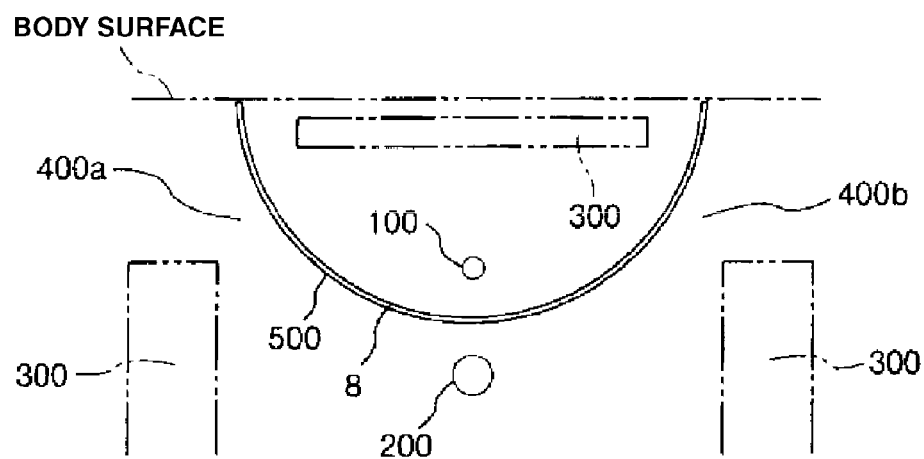
FIG. 11 is a cross-sectional view explaining an operating procedure of the puncture apparatus shown in FIG. 1.

Next, as shown in FIG. 11, the strings 91, 92 are pulled respectively by predetermined forces, the position of the implant 8 with respect to the urethra 100 is adjusted, unnecessary portions of the implant 8 are cut out, and afterward the procedure is completed.

As explained above, according to this puncture apparatus 1, when indwelling an implant, it is possible to make a correspondence only by a procedure exhibiting relatively low invasiveness, involving a puncture of the puncture needle 31 or the like, and it is not necessary to carry out a highly invasive incision or the like, so that the burden on the patient is relatively small and also, the safety of the patient is quite high.

Also, because the living body can be punctured by the puncture needle 31 by avoiding the urethra and the vaginal wall, it is possible to prevent a phenomenon in which the puncture needle 31 will puncture the urethra and will puncture the vaginal wall, thus facilitating a safe result. Also, it is possible for the operator himself to prevent a phenomenon in which his finger tip will be punctured by the puncture needle 31 and so safety can be obtained.

Also, it is possible to prevent a phenomenon in which, such as in a conventional case of incising a vagina, the implant is exposed to the inside of the vagina from a wound caused by the incision and in which complications occur which are caused by an infection from the wound or the like.

In this embodiment disclosed by way of example, the puncture hole formed for the patient by the puncture needle 31 is a through-hole, but it is not limited by this configuration and it is possible for the puncture hole not to employ a passing-through type.

Also, the urethral-insertion member is not limited to a tubular-shaped member and it is possible, for example, to employ a solid member, and in addition, it is also possible to employ a member which is hollow and in which either one or both of the distal portion and the proximal portion of the hollow member are occluded.

The distal portion of the urethral-insertion member can be provided with an expandable a contractible balloon as a restriction structure for restricting the position in the axial direction of the urethral-insertion member inside the urethra.

Also, in this embodiment, the puncture needle of the puncture member is a needle, the whole of which is bent in an arc shape. But the needle is not limited to this shape or configuration, and it is possible, for example, to employ a needle including a region bent in an arc shape only for a portion of the length of the needle. More specifically, it is enough if the puncture needle includes a region bent in an arc shape at least for a portion of the extent of the needle.

Also, it is sufficient if the puncture needle of the puncture member includes a bent region at least for a portion of its length and it is possible, for example, to employ a needle, the whole of which is bent in an elliptical arc shape and to employ a needle which includes a region bent in an elliptical arc shape only for a portion of its length. More specifically, it is possible for the puncture needle to include a region bent in an elliptical arc shape at least for a portion of its extent.

Figure 19A:
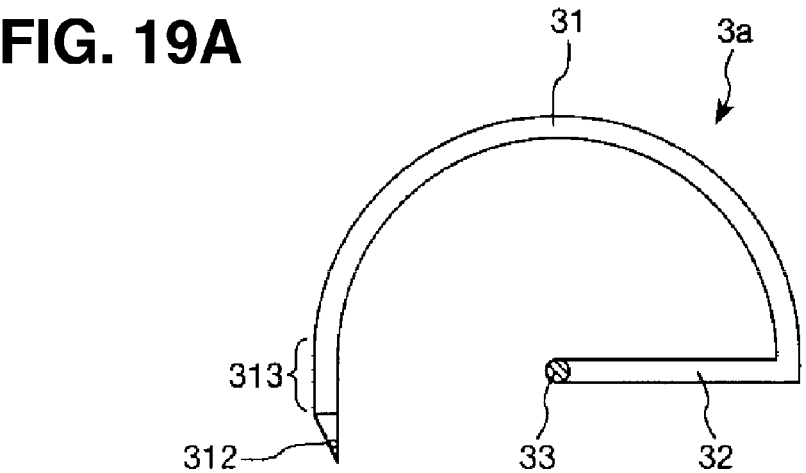
FIGS. 19A to 19C are cross-sectional views showing another example of the puncture member disclosed here.

Set forth next is a description of other examples of the puncture member disclosed here. The puncture needle 31 of the puncture member 3a shown in FIG. 19A includes a linear shaped portion 313 forming a linear shape at the distal portion of the needle. This linear-shaped portion 313 protrudes in the direction of a tangent line of the end portion of the needle from the end portion on the distal side of the arc of the puncture needle 31.

In case of using this puncture member 3a, before rotating the puncture member 3a, the puncture member 3a is first pressed against the patient and the linear shaped portion 313 of the puncture needle 31 punctures the patient.

Figure 19B:
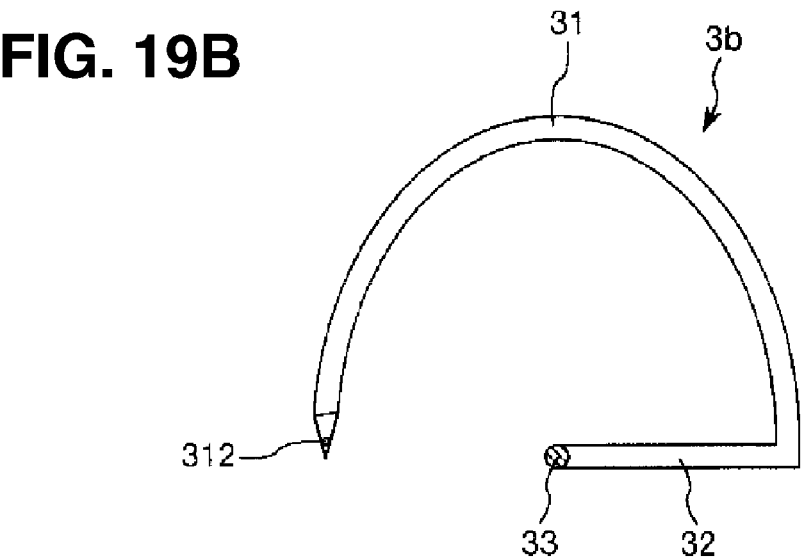

The puncture needle 31 of the puncture member 3b shown in FIG. 19B is bent in an elliptical arc shape centered on the axial portion 33. The long axis direction of the ellipse coincides with the up and down direction in FIG. 19B.

It is possible to use this puncture member 3b preferably in a case in which the urethra of the patient is positioned at a deep place from her body surface.

Figure 19C:
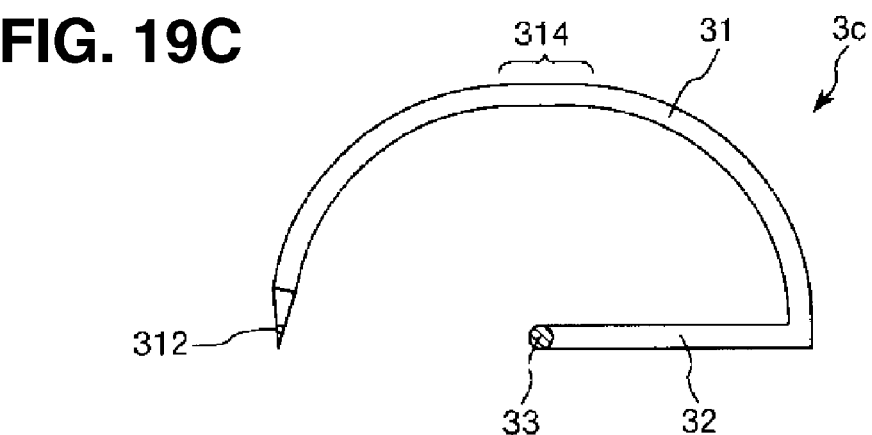

The puncture needle 31 of the puncture member 3c shown in FIG. 19C includes a linear shaped portion 314 forming a linear shape on the midway portion of the needle, that is, at the intermediate portion of the puncture needle 31.

It is possible to use this puncture member 3c preferably in a case in which the urethra of the patient is positioned at a shallow place from her body surface.

Figure 12:
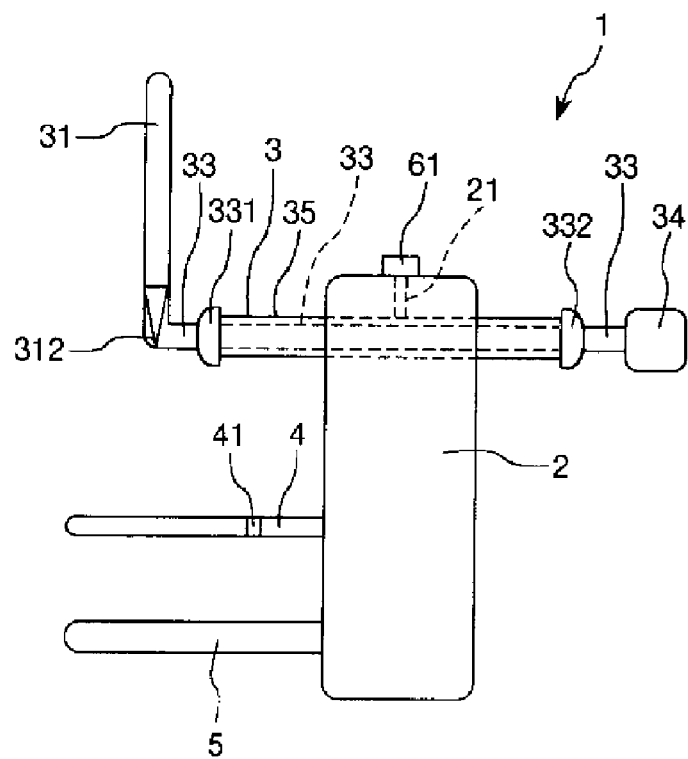
FIG. 12 is a side view of a second embodiment, disclosed by way of example, of a puncture apparatus disclosed here.

FIG. 12 illustrates a second embodiment representing another example of the puncture apparatus disclosed here. The following description of this embodiment will be set forth assuming that the left side in FIG. 12 is the "distal end" and the right side in FIG. 12 is the "proximal end".

The following description of the second embodiment will focus primarily on aspects or features of the puncture apparatus different from those of the first embodiment described above. Features and aspects of this second embodiment of the puncture apparatus that are similar to those described above in the first embodiment are identified by common reference numerals, and a detailed description of such aspects and features is not repeated.

As shown in FIG. 12, in the puncture apparatus 1' of the second embodiment, the axial portion 33 of the puncture member 3 is supported movably by the supporting member 2 in the axial direction of the axial portion 33, that is, in the axial direction of the urethral-insertion member 4.

Specifically, the puncture member 3 includes a tubular body 35 through which an axial portion 33 is inserted and which rotatably supports that axial portion 33. Also, the flanges 331, 332 are arranged on the distal side and on the proximal side of the tubular body 35 respectively, and owing to these flanges 331, 332, the movement in the axial direction of the axial portion 33 with respect to the tubular body 35 is blocked. That is, the flanges 331, 332 permit axial movement of the tubular body 35 relative to the supporting member 2, but limit the amount of such axial movement. The tubular body 35 is placed (mounted) on the supporting member 2 movably in the axial direction of the axial portion 33, that is, in the axial direction of the urethral-insertion member 4.

By moving the puncture member 3 in the axial direction of the urethral-insertion member 4, it is possible for the puncture needle 31 to be disposed in the axial direction of the urethral-insertion member 4 at any position, including on the proximal side of the distal-most tip of the urethral-insertion member 4, at the same position as that of the distal-most tip of the urethral-insertion member 4, and on the distal side of the distal-most end of the urethral-insertion member 4.

Also, the puncture apparatus 1' includes a male screw 61. At the positional region of the supporting member 2 corresponding to that of the tubular body 35, there is formed a female screw portion 21 having a female screw to threadably engage the male screw 61.

When rotating the male screw 61 in a predetermined direction, the distal end of that male screw 61 pressure-contacts the tubular body 35, and the movement of the tubular body 35 with respect to the supporting member 2 is blocked. Also, when rotating the male screw 61 in the reverse direction with respect to the abovementioned direction, the distal end of that male screw 61 is separated from the tubular body 35 and the movement of the tubular body 35 with respect to the supporting member 2 becomes possible.

The male screw 61 and the female screw portion 21 constitute a lock unit for changing-over between a state in which the tubular body 35 is movable with respect to the supporting member 2 and a state in which the movement of the tubular body 35 is blocked.

Also, on the outer circumferential surface of the tubular body 35, there is provided a scale which indicates a distance from a reference position of the center 311 of the puncture needle 31 in the axial direction of the axial portion 33 (regarding the center 311, see FIG. 2).

Also, the urethral-insertion member 4 is a solid bar-shaped member. The distal portion of the urethral-insertion member 4 is rounded. Thus, it is possible to insert the urethral-insertion member 4 smoothly into the inside of the urethra. Needless to say, it is possible for the urethral-insertion member 4 to be formed similarly as that of the first embodiment.

This second embodiment of the puncture apparatus 1' is able to obtain similar effects as those of the aforementioned first embodiment.

Figure 13:
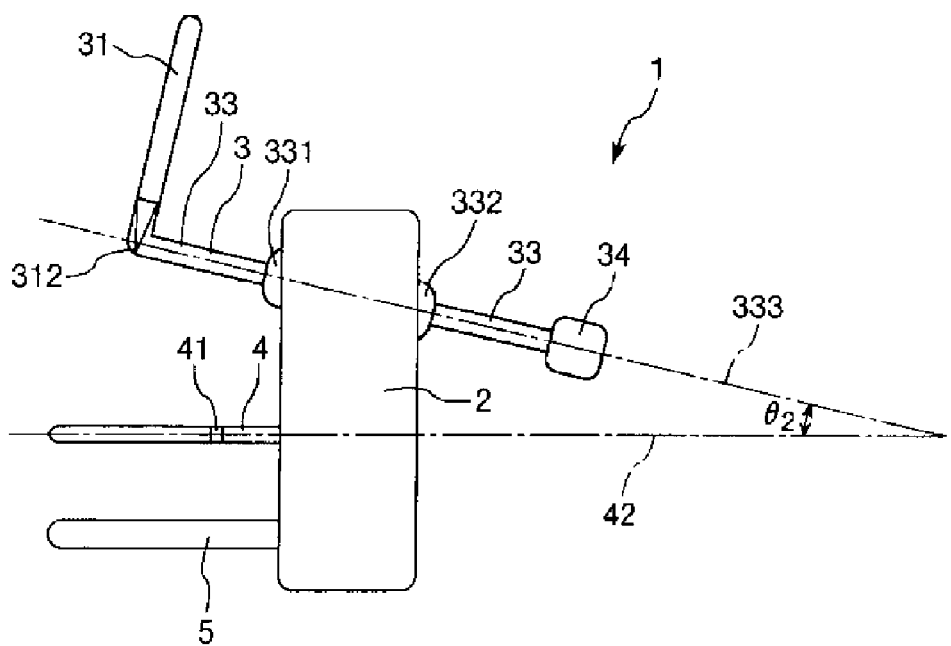
FIG. 13 is a side view of a third embodiment, disclosed by way of example, of a puncture apparatus disclosed here.

FIG. 13 illustrates a third embodiment representing another example of the puncture apparatus disclosed here. The following description of this embodiment will be set forth assuming that the left side in FIG. 13 is the "distal end" and the right side in FIG. 13 is the "proximal end".

The following description of the third embodiment will focus primarily on aspects or features of the puncture apparatus different from those of the first embodiment described above. Features and aspects of this embodiment that are similar to those described above in the first embodiment are identified by common reference numerals, and a detailed description of such aspects and features is not repeated.

As shown in FIG. 13, in the puncture apparatus 1" of the third embodiment, the axis 333 of the axial portion 33 of the puncture member 3 is inclined with respect to the axis 42 such that the distance of separation between the axis 333 and the axis 42 of the urethral-insertion member 4 increases toward the distal side. Thus, it is possible to bury the implant 8 by being inclined.

The axis 42 of the urethral-insertion member 4 and the axis of the vaginal-insertion member 5 are parallel, and the axis 333 of the axial portion 33 of the puncture member 3 is inclined with respect to the axis of the vaginal-insertion member 5 such that the distance of separation between the axis 333 and the axis of the vaginal-insertion member 5 increases toward the distal side.

It is preferable for the inclination-angle θ2 of the axis 333 with respect to the axis 42 to be around 20° to 60°, more preferably around 30° to 45°, and still more preferably around 35° to 40°. Thus, it is possible to carry out the puncture of the puncture needle 31 relatively easily, and concurrently it is possible to realize a shorter puncture-distance.

To explain in more detail, by setting the inclination angle θ2 to be within the aforesaid range, it is possible for the puncture needle 31 to widely capture the right-left obturator foramens 400a, 400b of the pelvis planarly and it is possible to widely secure the puncture space of the puncture needle 31. More specifically, in a state of setting the patient to be at a predetermined body position (dorsosacral position), it is possible to puncture the puncture needle 31 comparatively toward the perpendicular direction with respect to the right-left obturator foramens 400a, 400b of the pelvis. Therefore, it is possible to carry out the puncture of the puncture needle 31 rather easily. In addition, by puncturing the puncture needle 31 comparatively toward perpendicular direction with respect to the obturator foramens 400a, 400b, the puncture needle passes a shallow portion of the tissue, so that it is possible for the needle tip of the puncture needle 31 to pass between the right-left obturator foramens 400a, 400b by a shorter distance. It is possible for the puncture needle 31 to pass comparatively near the pubic-bone connection of the obturator foramens 400a, 400b and preferably through a safety zone, so that it is possible to puncture the region safely in which there are fewer nerves or blood vessels for avoiding injuries. Therefore, there can be obtained a state of lower invasion and it is possible to burden the patient to a lesser degree. In this manner, by setting the inclination angle θ2 in the aforesaid range, it is possible to carry out the puncture of the puncture needle 31 to the patient more properly. On the other hand, in a case in which the inclination angle θ2 is less than the aforesaid lower limit or exceeds the aforesaid upper limit, depending on the individual differences of the patients, the postures during the procedures and the like, there can occur a situation in which it is not possible for the puncture needle 31 to widely capture the obturator foramens 400a, 400b planarly, a situation in which it is not possible to shorten the puncture path adequately and so on. Therefore, it is preferable for the puncture needle 31 to be punctured toward the perpendicular direction with respect to the right-left obturator foramens 400a, 400b of the pelvis.

Also, by carrying out the puncture in the abovementioned angle, it becomes easier to aim the tissue between the mid-urethra indicating the middle positional portion in the length direction of the urethra and the vagina. The position between the mid-urethra and the vagina is a position suitable as the region at which the implant 8 is to be buried and the treatment of the urinary incontinence is to be carried out. More preferably, if the puncture is carried out in a state of manipulating the position so as to arrange a position of the urethra or the vagina, or both, it is rather easy to puncture a position between the mid-urethra and the vagina. It is preferable to move the urethra or the vagina, or both to the predetermined position before passing the puncture member at the position between the mid-urethra and vagina.

Moving the urethra or the vagina, or both may be for example pressing/pulling toward the inside/outside of the body. The means for pushing-in either one of the urethra and the vagina toward the inside of the body moves, for example, the urethral-insertion member 4 and/or the vaginal insertion member 5 toward the inside of the body before the puncture as far as a predetermined position along each of the axes after setting a state in which the insertion member is inserted to a proper position. The urethral-insertion member 4 and/or the vaginal insertion member 5 may have a suction mechanism for sucking the inner wall of the urethra or the vagina. The suction mechanism may hold the position of the urethral-insertion member 4 and/or the vaginal insertion member 5. When the urethral-insertion member 4 and/or the vaginal insertion member 5 may be moved toward the inside or the outside of the body, the urethra and/or the vagina may be moved along the member 4 and/or the member 5. At that time, by attaching a visible marker or such a marker which can be imaged under a noninvasive monitoring of the inside of the body depending on such as X-ray, ultrasound or the like onto the urethral-insertion member 4 and/or onto the vaginal insertion member 5, it is possible to recognize the movement distance of the member.

By puncturing the puncture needle 31 perpendicularly with respect to the right-left obturator foramens 400a, 400b of the pelvis in a state in which the position is prolapsed so as to press at least one of the urethra and the vagina toward the inside of the body, it is possible to form the path at a position suitable for the indwelling of the implant 8.

It is preferable that the orbit of the puncture needle 31 is set so as to pass the safety zone of the right-left obturator foramens 400a, 400b of the pelvis, that at least one of the urethra and the vagina is prolapsed toward the inside of the body such that the orbit is positioned between the mid-urethra and the vagina, and that the path will be formed by executing the puncture along the orbit of the puncture needle 31.

The urethral-insertion member 4 is a solid bar-shaped member. Also, the distal portion of the urethral-insertion member 4 is rounded. Thus, it is possible to insert the urethral-insertion member 4 smoothly into the inside of the urethra. It is possible for the urethral-insertion member 4 to be formed similarly as that of the first embodiment.

The puncture apparatus 1″ according to this third embodiment is able to obtain similar effects as those of the first embodiment described above.

It is possible for the axis 42 of the urethral-insertion member 4 and the axis of the vaginal-insertion member 5 not to be parallel to each other.

Figure 20:
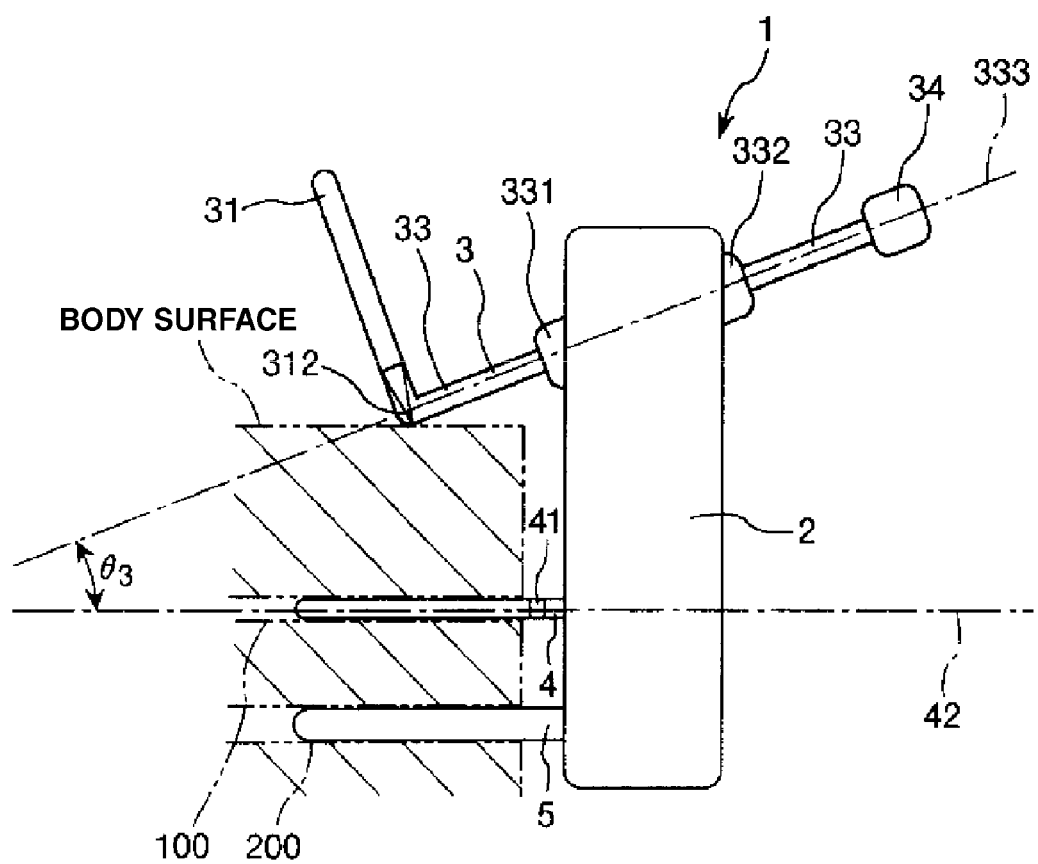
FIG. 20 is a side view of a fourth embodiment, disclosed by way of example, of a puncture apparatus disclosed here.

FIG. 20 illustrates a fourth embodiment representing another example of the puncture apparatus disclosed here. The following description of this embodiment will be set forth assuming that the left side in FIG. 20 is the "distal end" and the right side in FIG. 20 is the "proximal end".

The following description of the fourth embodiment will focus primarily on aspects or features of the puncture apparatus different from those of the third embodiment described above. Features and aspects of this fourth embodiment of the puncture apparatus that are similar to those described above are identified by common reference numerals, and a detailed description of such aspects and features is not repeated.

As shown in FIG. 20, in the puncture apparatus 1‴ of the fourth embodiment, the axis 333 of the axial portion 33 of the puncture member 3 is inclined with respect to the axis 42 such that the distance of separation between the axis 333 and the axis 42 of the urethral-insertion member 4 decreases toward the distal side. Thus, it is possible to bury the implant 8 by being inclined.

The axis 42 of the urethral-insertion member 4 and the axis of the vaginal-insertion member 5 are in parallel and the axis 333 of the axial portion 33 of the puncture member 3 is inclined with respect to the axis of the vaginal-insertion member 5 such that the separated distance between the axis 333 and the axis of the vaginal-insertion member 5 decreases toward the distal side.

The preferable range of the inclination-angle θ3 of the axis 333 with respect to the axis 42 is similar to the preferable range of the inclination-angle θ2 of the third exemplified embodiment.

This puncture apparatus 1''' is able to obtain similar effects as those described above regarding the third embodiment.

Note that the axis 42 of the urethral-insertion member 4 and the axis the vaginal-insertion member 5 are allowed to be not in parallel.

Figure 21:
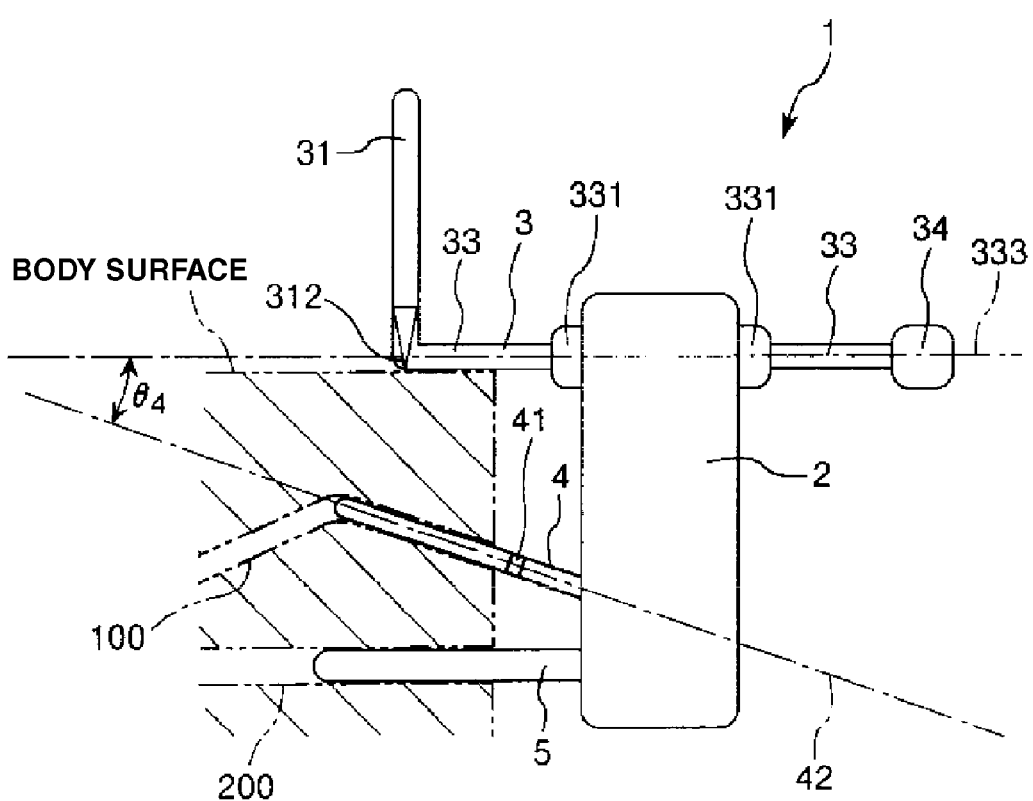
FIG. 21 is a side view of a fifth embodiment, disclosed by way of example, of a puncture apparatus disclosed here

FIG. 21 illustrates a fifth embodiment representing another example of the puncture apparatus disclosed here. The following description of this embodiment will be set forth assuming that the left side in FIG. 21 is the "distal end" and the right side in FIG. 21 is the "proximal end".

The following description of the fifth embodiment will focus primarily on aspects or features of the puncture apparatus different from those of the third embodiment described above. Features and aspects of this embodiment that are similar to those described above in the third embodiment are identified by common reference numerals, and a detailed description of such aspects and features is not repeated.

As shown in FIG. 21, in the puncture apparatus 10 of the fifth embodiment, the axis 42 of the urethral-insertion member 4 is inclined with respect to the axis 333 such that the distance of separation between the axis 42 and the axis 333 of the axial portion 33 of the puncture member 3 decreases toward the distal side. In other words, the axis 333 of the axial portion 33 of the puncture member 3 is inclined with respect to the axis 42 such that the distance of separation between the axis 333 and the axis 42 of the urethral-insertion member 4 decreases toward the distal side. Thus, it is possible to bury the implant 8 by being inclined.

The axis 333 of the axial portion 33 of the puncture member 3 and the axis of the vaginal-insertion member 5 are parallel, and the axis 42 of the urethral-insertion member 4 is inclined with respect to the axis of the vaginal-insertion member 5 such that the distance of separation between the axis line 333 and the axis line of the vaginal-insertion member 5 increases toward the distal side.

The preferable range of the inclination-angle θ4 of the axis line 42 with respect to the axis 333 (inclination-angle of the axis 333 with respect to the axis 42) is similar to the preferable range of the inclination-angle θ2 discussed above regarding the third embodiment.

This puncture apparatus 10 is able to obtain similar effects as those described above regarding the third embodiment.

It is possible for the axis 42 of the urethral-insertion member 4 to be inclined with respect to the axis 333 such that the distance of separation between the axis 42 and the axis 333 of the axial portion 33 of the puncture member 3 increases toward the distal side. In other words, it is possible for the axis 333 of the axial portion 33 of the puncture member 3 to be inclined with respect to the axis 42 such that the distance of separation between the axis 333 and the axis 42 of the urethral-insertion member 4 increases toward the distal side.

FIGS. 14-18 illustrate a sixth embodiment representing another example of the puncture apparatus disclosed here.

Figure 14:
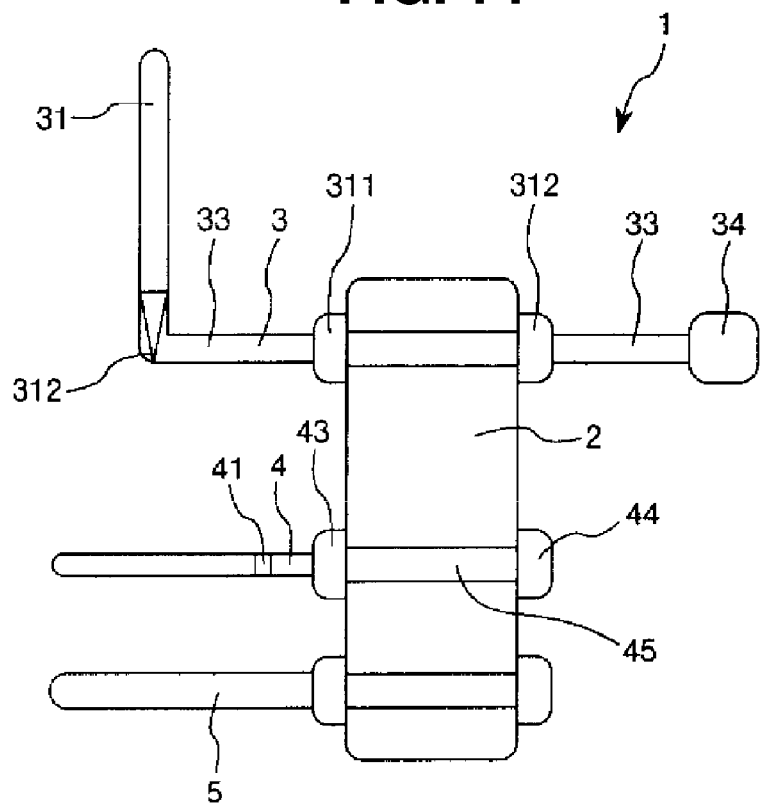
FIG. 14 is a side view of a sixth embodiment, disclosed by way of example, of a puncture apparatus disclosed here.
Figure 15:
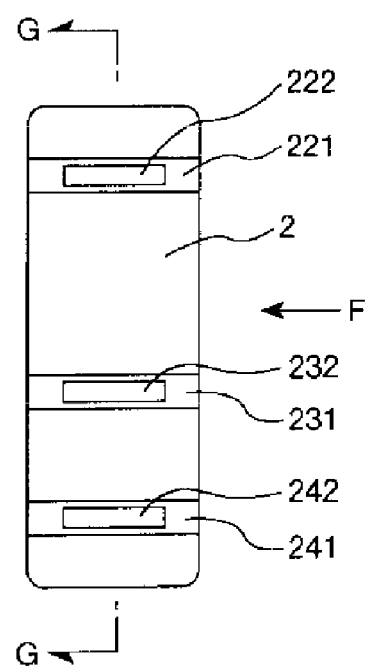
FIG. 15 is a side view showing a supporting member of the puncture apparatus shown in FIG. 14.
Figure 16A:
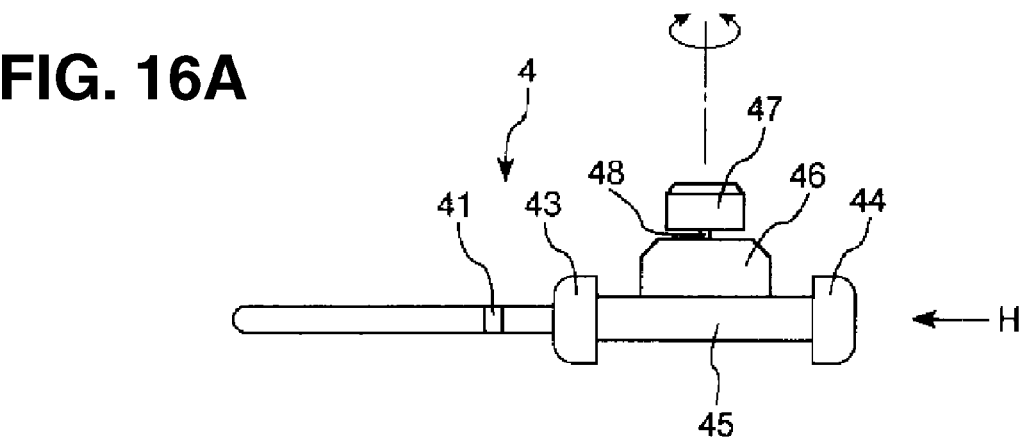
FIGS. 16A to 16C are views showing a urethral-insertion member of the puncture apparatus shown in FIG. 14.
Figure 16B:
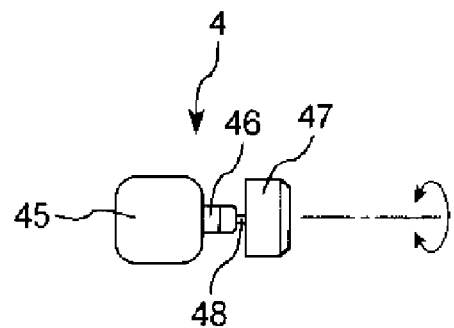
Figure 16C:
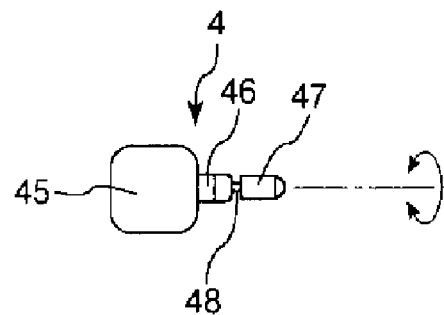
Figure 17:
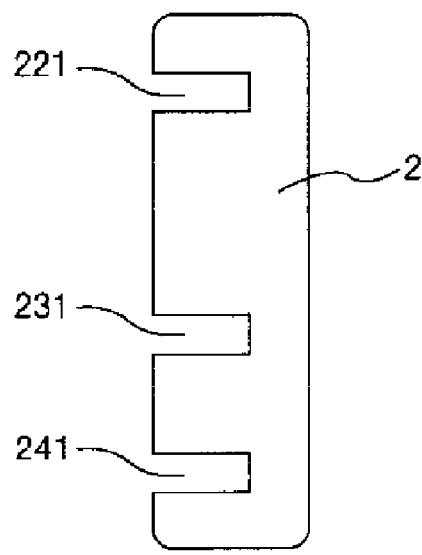
FIG. 17 is a view seeing the puncture apparatus from a direction of an arrow 17 shown in FIG. 15.

FIG. 16A is a front elevational view, that is, a view seen from the upside in FIG. 14. Also, either one of FIG. 16B and FIG. 16C is a view seen from a direction of an arrow 16B, 16C in the urethral-insertion member shown in FIG. 16A, in which for the attachment piece of the urethral-insertion member shown in FIG. 16C, there is shown a state thereof in which the attachment piece is rotated by 90° with respect to the attachment piece of the urethral-insertion member shown in FIG. 16B. The following explanation is set forth assuming that the left side in FIG. 14, FIG. 15, FIG. 16A is the "distal end" and the right side is the "proximal end".

The following description of the sixth embodiment will focus primarily on aspects or features of the puncture apparatus different from those of the first embodiment described above. Features and aspects of this embodiment that are similar to those described above in the first embodiment are identified by common reference numerals, and a detailed description of such aspects and features is not repeated.

In the puncture apparatus 10' of the sixth embodiment shown in FIG. 14, the puncture member 3, the urethral-insertion member 4 and the vaginal-insertion member 5 are freely detachable with respect to supporting member 2 respectively. More specifically, the axial portion 33 of the puncture member 3, the urethral-insertion member and the vaginal-insertion member 5 are supported by the supporting member 2 in a freely detachable manner respectively.

Also, the urethral-insertion member 4 is a solid bar-shaped member, and the distal portion of the urethral-insertion member 4 is rounded. Thus, it is possible to insert the urethral-insertion member 4 smoothly into the inside of the urethra. Needless to say, it is possible for the urethral-insertion member 4 to be formed similar to that of the first embodiment described above.

As shown in FIG. 14, FIG. 15, FIG. 17 and FIG. 18, the supporting member 2 includes a groove 221 to which the puncture member 3 is attached or in which the puncture member 3 is positioned; a through-hole 222 provided in the inside of the groove 221; a groove 231 to which the urethral-insertion member 4 is attached or in which the urethral-insertion member 4 is positioned; a through-hole 232 provided in the inside of the groove 231; a groove 241 to which the vaginal-insertion member 5 is attached or in which the vaginal-insertion member 5 is positioned; and a through-hole 242 provided in the inside of the groove 241. The grooves 221, 231, 241 are formed respectively on the front side of the supporting member 2 in the FIG. 15 illustration and extend from the distal end to the proximal end of the supporting member 2.

The construction or configuration of the detachable mechanisms of the puncture member 3, the urethral-insertion member 4 and the vaginal-insertion member 5 with respect to the supporting member 2 is similar to one another, so that hereinafter, with regard to each detachable arrangement, the detachable mechanism of the urethral-insertion member 4 will be explained representatively.

As shown in FIG. 14 and FIG. 16, in a state of being attached to the supporting member 2 (hereinafter, also referred to as "attachment state"), the urethral-insertion member 4 is formed with a flange 43 and a flange 44 on the distal side and on the proximal side respectively through that supporting member 2, and the axial movement of the urethral-insertion member 4 with respect to the supporting member 2 is blocked by these flanges 43, 44. The flange 44 is arranged at the proximal portion of the urethral-insertion member 4.

Also, a region 45 between the flange 43 and the flange 44 of the urethral-insertion member 4 is thicker than the region on the distal side from the flange 43 of the urethral-insertion member 4. Also, the cross-sectional shape of the region 45 between the flange 43 and the flange 44 of the urethral-insertion member 4 is square shape according to the constitution shown in the drawing.

At the region 45 between the flange 43 and the flange 44 of the urethral-insertion member 4, there is formed a protruding portion 46, in the attachment state, which protrudes toward the rear side from the front side of the drawing of FIG. 14, that is, which protrudes toward the upper side in FIG. 16A. At the protruding portion 46, there is located an attachment piece 48 through a freely rotatable axis member 47. This attachment piece 48 has a flattened shape. The attachment piece 48 protrudes toward the upper side in FIG. 16A.

When attaching the urethral-insertion member 4 to the supporting member 2, the attachment piece 48 of the urethral-insertion member 4 is set in a state shown in FIG. 16C and the attachment piece 48 is inserted from the groove 231 of the supporting member 2 and is passed through the through-hole 232. Then, at that time, the region 45 between the flange 43 and the flange 44 of the urethral-insertion member 4 is inserted into the groove 231 of the supporting member 2 and concurrently, the protruding portion 46 is inserted into the through-hole 232.

Figure 18:
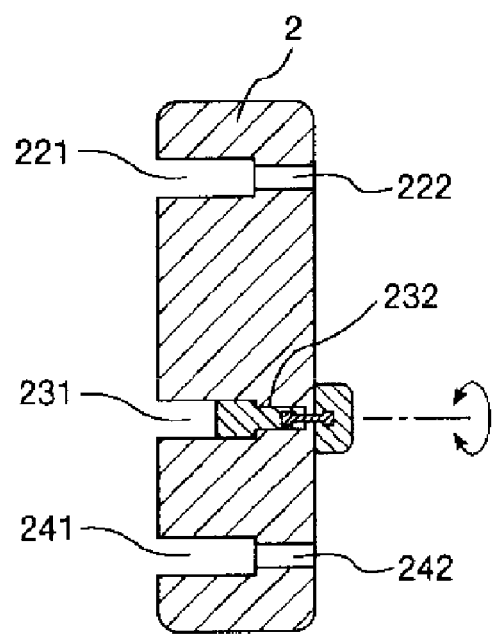
FIG. 18 is a cross-sectional view along the section line 18-18 in FIG. 15.

Next, as shown in FIG. 18, the attachment piece 48 of the urethral-insertion member 4 is set in a state shown in FIG. 16B by being rotated by 90°. Thus, while the region 45 between the flange 43 and the flange 44 of the urethral-insertion member 4 is attached onto or set into the bottom surface of the groove 231, the attachment piece 48 is attached or set onto the surface on the right side of the urethral-insertion member 4 in FIG. 18 and so the attachment and detachment of the urethral-insertion member 4 with respect to the supporting member 2 is blocked.

Also, when removing the urethral-insertion member 4 from the supporting member, the attachment piece 48 of the urethral-insertion member 4 is set in a state shown in FIG. 16C and the urethral-insertion member 4 is made to move toward the left side in FIG. 18. Thus, it is possible to remove the urethral-insertion member 4 from the supporting member 2.

This puncture apparatus 10' is able to obtain similar effects as those of the first embodiment described above. It is possible to apply this sixth embodiment to the second to fifth embodiments described above to provide the freely detachable arrangement of the puncture member 3, the urethral-insertion member 4 and/or the vaginal-insertion member 5 with respect to the supporting member 2.

In this embodiment, the puncture member 3, the urethral-insertion member 4 and the vaginal-insertion member 5 are freely detachable with respect to the supporting member 2. But the apparatus is not limited to this configuration and it is possible, for example, for only one or only two of the puncture member 3, urethral-insertion member 4 and the vaginal-insertion member 5 to be freely detachable with respect to the supporting member 2. In this case, it is preferable for at least the puncture member 3 to be freely detachable with respect to the supporting member 2.

Figure 22A:
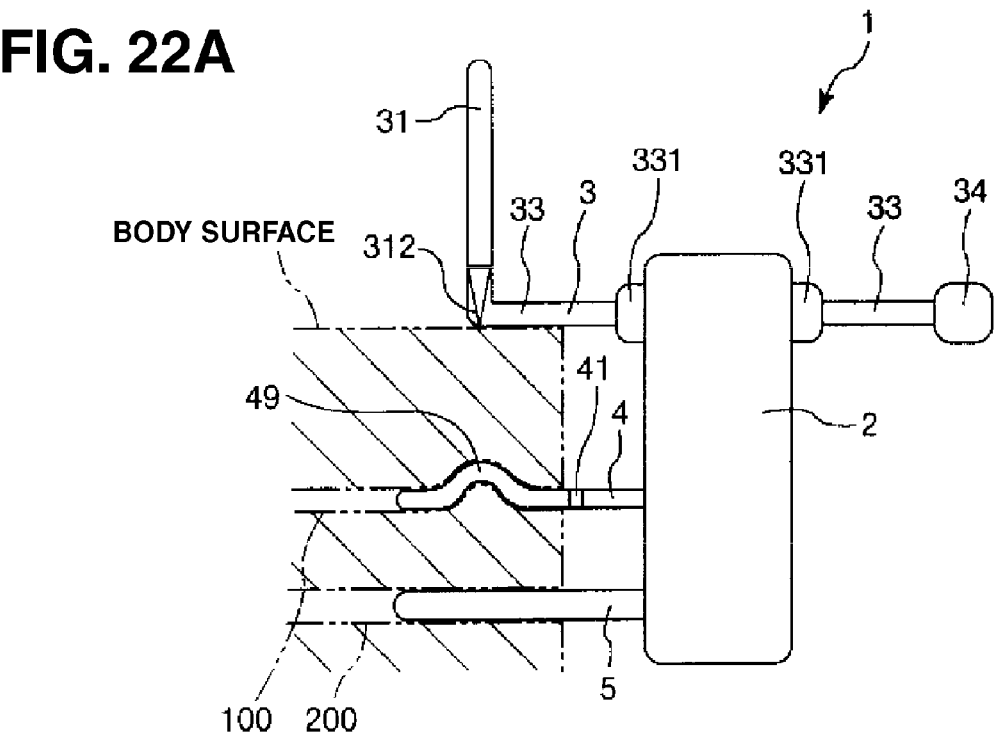
FIGS. 22A to 22C are side views of a seventh embodiment, disclosed by way of example, of a puncture apparatus disclosed here
Figure 22B:
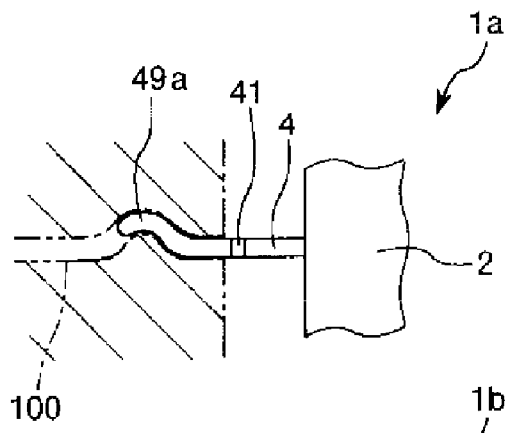
Figure 22C:
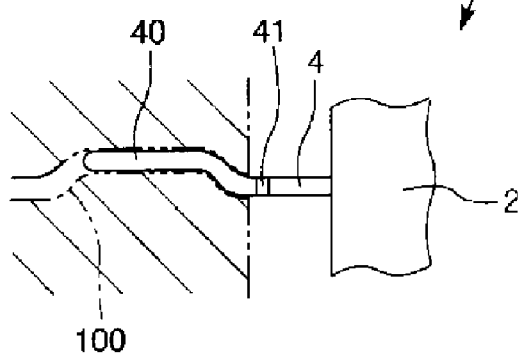

FIGS. 22A-22C illustrates a seventh embodiment representing another example of the puncture apparatus disclosed here. The following description of this embodiment will be set forth assuming that the left side in FIGS. 22A-22C is the "distal end" and the right side in FIGS. 22A-22C is the "proximal end".

The following description of the seventh embodiment will focus primarily on aspects or features of the puncture apparatus different from those of the first embodiment described above. Features and aspects of this embodiment that are similar to those described above in the first embodiment are identified by common reference numerals, and a detailed description of such aspects and features is not repeated.

As shown in FIG. 22A, in the puncture apparatus 10' of the seventh embodiment, the urethral-insertion member 4 is configured so that a midway portion of the urethral-insertion member 4 is bent and includes a protruding portion 49 which protrudes toward the direction away from the vaginal-insertion member 5.

It is possible by this protruding portion 49 to widen the distance between the urethra 100 and the vagina 200 and thus, it is possible to reliably prevent a phenomenon in which the puncture needle 31 will puncture the urethra 100 or the vaginal wall of the vagina 200. Similar effects are obtained by the puncture apparatuses 10'a, 10'b described below.

In the puncture apparatus 10'a shown in FIG. 22B, the length of the urethral-insertion member 4 becomes short with respect to that of the puncture apparatus 10' shown in FIG. 22A and there is included a protruding portion 49a at the distal portion of the urethral-insertion member 4. The protruding portion 49a is a portion which is formed by bending the urethral-insertion member 4 and which protrudes toward the direction apart from the vaginal-insertion member 5, in which it is constituted to be shorter than the protruding portion 49 of the puncture apparatus 1.

In this puncture apparatus 10'a, it is possible to prevent an excessive insertion of the urethral-insertion member 4 into the urethra 100.

In the puncture apparatus 10'b shown in FIG. 22C, the urethral-insertion member 4 includes a linear shaped portion 40 forming a linear shape which is positioned at the regional portion from the midway to the distal end thereof and which is on the side apart from the vaginal-insertion member 5 compared with the proximal portion. Note that there is no limitation in particular for the length of the linear shaped portion 40 and the length is set arbitrarily in response to various conditions.

These puncture apparatuses 10', 10'a, 10'b are able to obtain similar effects as those described above regarding the first embodiment. And it is possible to apply this seventh embodiment to the other respective embodiments described above.

Figure 23:
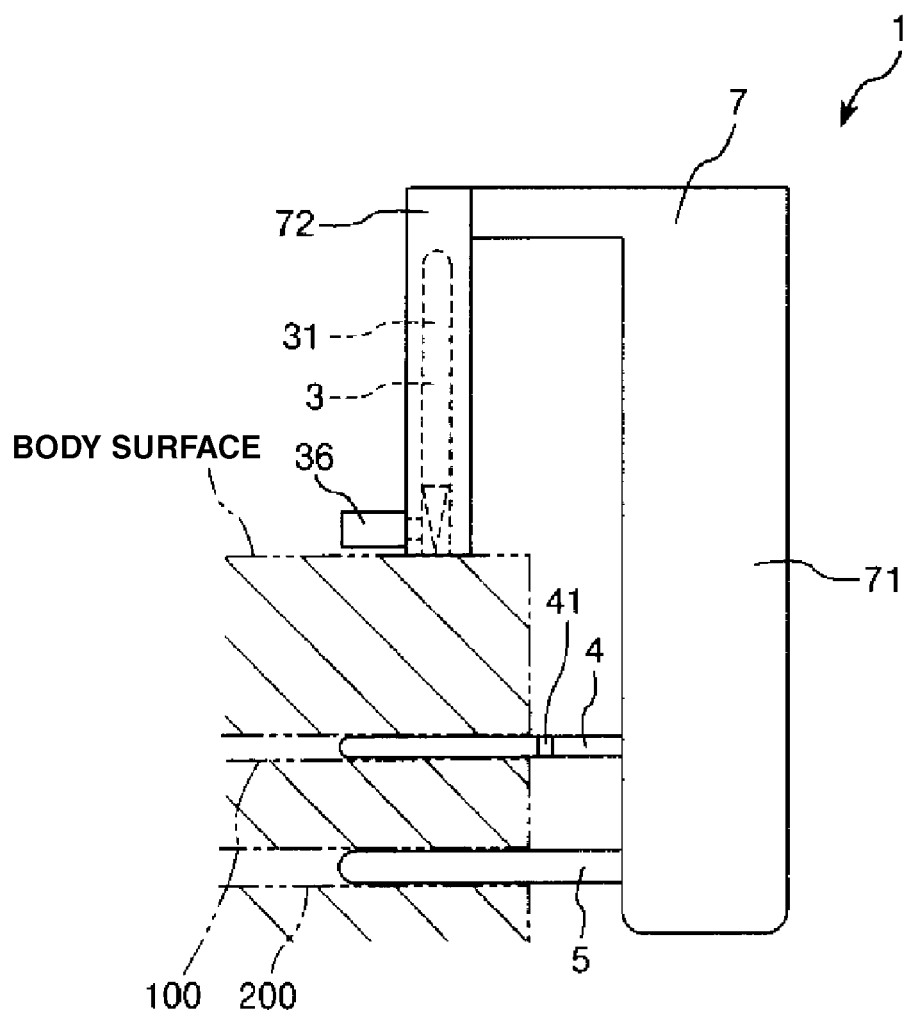
FIG. 23 is a side view of an eighth embodiment, disclosed by way of example, of a puncture apparatus disclosed here
Figure 24:
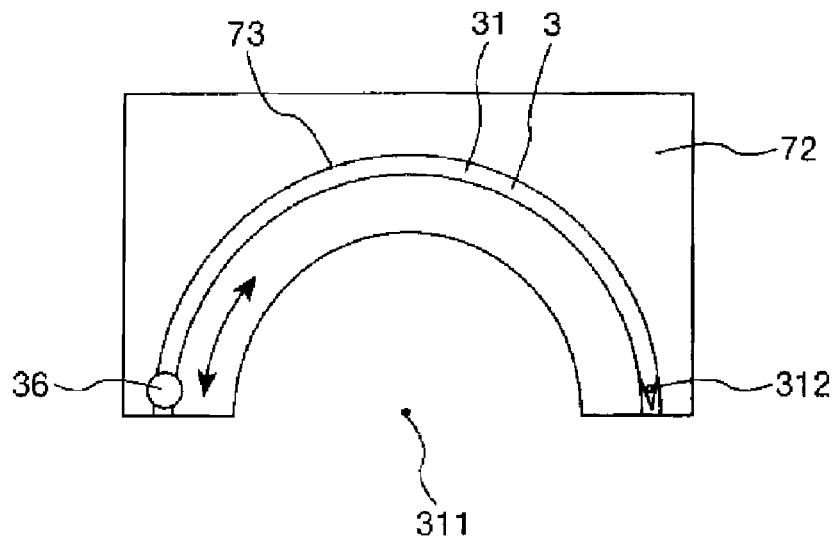
FIG. 24 is a front elevational view showing a puncture member and a second supporting portion of the puncture apparatus shown in FIG. 23.

FIGS. 23 and 24 illustrate an eighth embodiment representing another example of the puncture apparatus disclosed here, with FIG. representing a side view of the apparatus and FIG. 24 showing a puncture member and a second supporting portion of the puncture apparatus shown in FIG. 23 as seen from the front. The following description of this embodiment will be set forth assuming that the left side in FIG. 23 is the "distal end" and the right side in FIG. 23 is the "proximal end".

The following description of the eighth embodiment will focus primarily on aspects or features of the puncture apparatus different from those of the first embodiment described above. Features and aspects of this embodiment that are similar to those described above in the first embodiment are identified by common reference numerals, and a detailed description of such aspects and features is not repeated.

As shown in FIG. 23 and FIG. 24, in the puncture apparatus 10" of the eighth embodiment, a supporting member (restriction means) 7 includes a first supporting portion 71 for supporting the urethral-insertion member 4 and the vaginal-insertion member 5; and a second supporting portion 72 on the distal side of the first supporting portion 71 and which freely rotatably supports the puncture member 3.

The puncture member 3 includes a puncture needle 31 and a grasping unit 36 provided at the proximal portion of the puncture needle 31. The grasping unit 36 protrudes toward the distal side from the proximal portion of the puncture needle 31, that is, toward the left side in FIG. 23.

In the second supporting portion 72, there is formed a groove (arc-shaped groove) 73 having a shape corresponding to the puncture needle 31, and the puncture needle 31 is inserted (housed) inside the groove 73 in a freely rotatable or freely movable manner. More specifically, the puncture needle 31 is configured and housed to slide along the inner surface of the groove 73, and the puncture needle 31 moves rotationally (along an arc), with the center 311 serving as the rotary center by sliding along the inner surface of the groove 73. The second supporting portion 72 thus serves as a guide member for guiding the puncture needle 31 along the groove 73. When moving the puncture needle 31, that is, the puncture member 3 rotationally, the grasping unit 36 is grasped and the rotational operation of the puncture member is carried out. Regarding the center 311, it is possible to apply the features of axial portion 33 in the other embodiments.

The inside of the groove 73 is larger than the opening of the entrance to the groove. It is thus possible to prevent the puncture needle 31 from dropping-out from the inside of the groove 73 (e.g., by configuring the portion of the needle positioned in the groove to be slightly larger than the size of the opening of the entrance of the groove).

This puncture apparatus 10″ obtains similar effects as those described above regarding the first embodiment. It is possible to apply this eighth embodiment to the respective other embodiments described above.

The guide member is not limited to the specific member used in this embodiment. It is possible, for example, to employ members described below and referred to as constitution 1, constitution 2 and constitution 3.

In constitution 1, a convex portion (guide portion) is provided on the puncture needle, the puncture needle is not housed in the groove of a guide member, the convex portion is housed in the guide member, and this convex portion is guided along the groove.

In constitution 2, the guide member includes, for example, a rail (rib) forming an arc shape, and there is provided, on the puncture needle, a guide portion which is engaged with the rail and which is movable along this rail. The guide portion is guided along the rail.

In constitution 1, the guide member includes a plurality of pin-pairs constituted by pin-pairs each of which is arranged by being separated as much as a predetermined distance, for example, a distance which is a little bit longer than the outer diameter of the puncture needle and the puncture needle is configured to move between each of the pin-pairs. The respective pin pairs are arranged, for example, in an arc shape and the puncture needle is guided by these respective pin-pairs.

Figure 25:
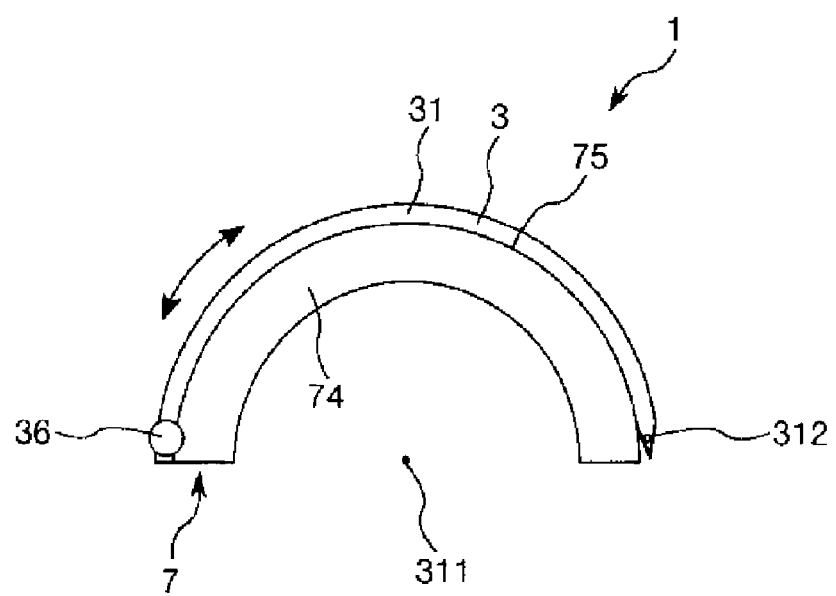
FIG. 25 is a front elevational view showing a puncture member and a second supporting portion of a supporting member in a ninth embodiment of the puncture apparatus disclosed here.

FIG. 25 illustrates a puncture member and a second supporting portion of a supporting member in a ninth embodiment of the puncture apparatus disclosed here. In the description below, the upper side in FIG. 25 is "up" and the lower side is "down".

The following description of the ninth embodiment will focus primarily on aspects or features of the puncture apparatus different from those of the eighth embodiment described above. Features and aspects of this embodiment that are similar to those described above in the eighth embodiment are identified by common reference numerals, and a detailed description of such aspects and features is not repeated.

As shown in FIG. 25, in the puncture apparatus 10‴ in the ninth embodiment, a second supporting portion 74 of the supporting member 7 forms an arc shape. More specifically, an upper surface 75 of the second supporting portion 74 forms a shape corresponding to the puncture needle 31.

Also, the puncture needle 31 is placed or positioned on the upper surface 75 of the second supporting portion 74. The puncture needle 31 is slidable along the upper surface 75 of the second supporting portion 74, and the puncture needle 31 moves rotationally (along an arc) by making the center 311 thereof as the rotary center by sliding along the upper surface 75. The second supporting portion 72 thus constitutes the guide member.

This puncture apparatus 10‴ is able to obtain similar effects as those described above regarding the eighth embodiment. And it is possible to apply this ninth embodiment to the respective other embodiments described above.

As described above, the puncture apparatus disclosed here is explained based on the embodiments shown in the drawings, but the present invention is not limited by these embodiments, and it is possible to replace the constitution of each portion by a different or arbitrary constitution having a similar function. It is also possible to add other arbitrary constituent elements.

Figure 26:
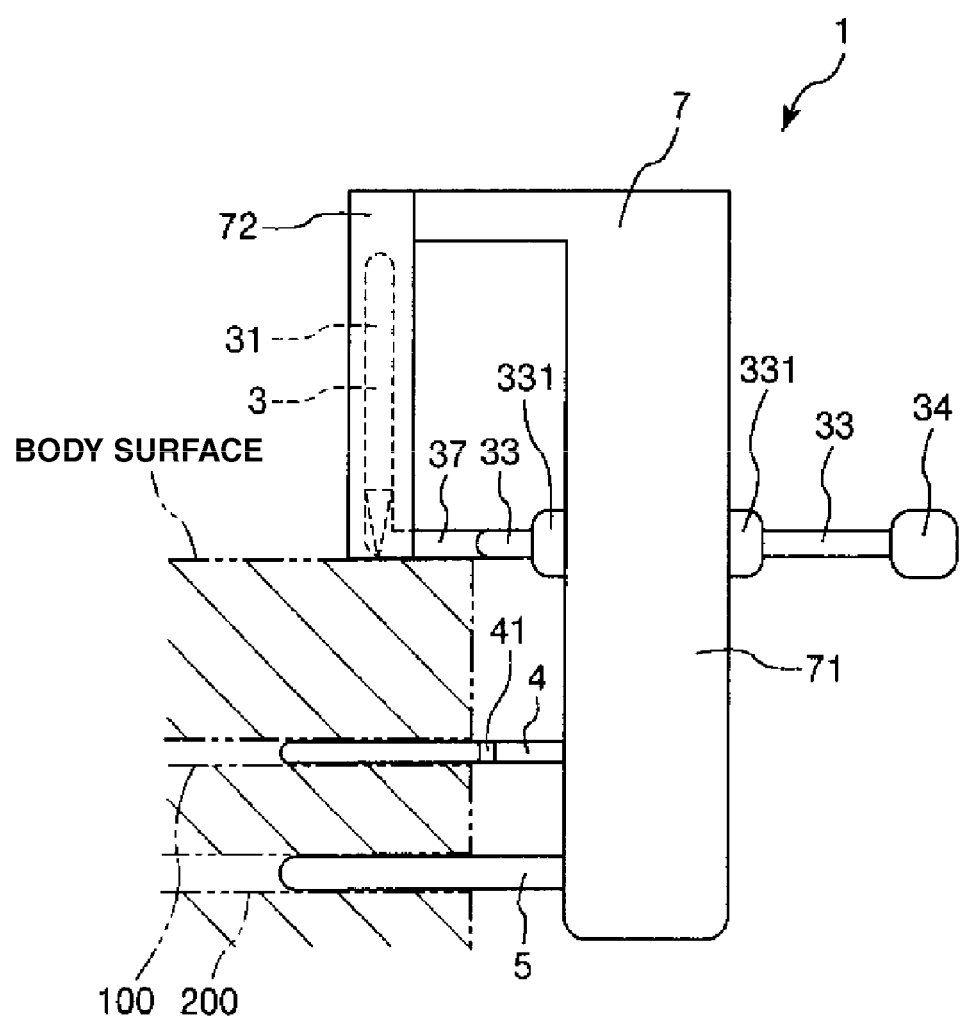
FIG. 26 is a side view showing another example of the puncture apparatus of the present invention.
Figure 27:
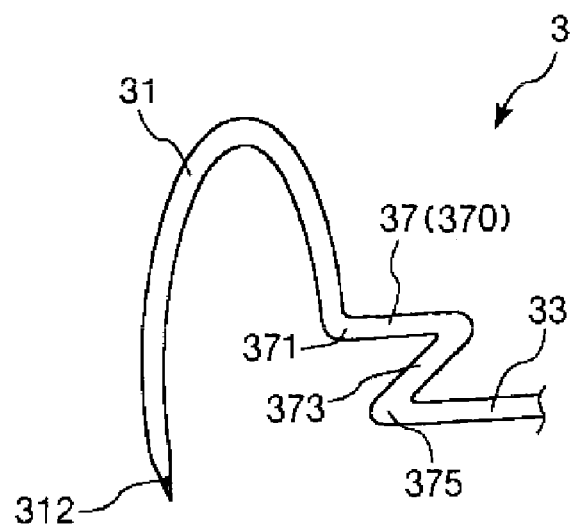
FIG. 27 is a perspective view showing a puncture member of the puncture apparatus shown in FIG. 26.

Also, it is possible to employ an arrangement in which two or more constructions or constitutions within the respective embodiments are combined. In particular, as shown in FIG. 26, by combining the first embodiment (see FIG. 1 and FIG. 2) and the eighth embodiment (see FIG. 23 and FIG. 24) and by providing the second supporting portion 72 of the eighth embodiment, which supports the puncture member 3 in a freely rotatable manner, in the puncture apparatus 1 of the first embodiment, it is possible to restrict the orbit exactly when puncturing the living body tissue by the puncture member 3 and thus, a more accurate puncture becomes possible. The interlock portion 37 of the puncture member 3 of the puncture apparatus 1, which is shown in this FIG. 26, forms an L-shape as shown in FIG. 27. The axial portion 33 of the puncture member 3 is located or mounted on the first supporting portion 71 in a freely rotatable manner.

Here, depending on the patient, the region, between the position at which the puncture needle 31 is inserted into (enters) the body from the body surface and the position at which the needle protrudes back outside the body from the body surface, rises and the center of the arc of the puncture needle 31 is positioned at the patient side compared with the body surface of the patient, so that there may be a situation in which the puncture apparatus 1 cannot be correctly placed at a predetermined position. Such a rising can be seen many times for heavy patients. On the other hand, for a skinny patient or the like, caused by the fact that the interlocking region or the vicinity of such region is depressed, it becomes a state in which there occurs a phenomenon of rising relatively and there occurs a situation in which the center portion of the patient interferes with the puncture needle 31, so that a situation arises in which that state prevents the puncture operation. Even in such a case, by setting the interlock portion 37 to be in an L-shape, it is possible to help prevent the interlock portion 37 and the axis portion 33 from interfering with the rising region of the patient and it is possible to carry out the puncture operation by the puncture needle 31 rather easily and also reliably. The interlock portion 37 is composed of a distal portion 371 and a proximal portion 373.

The distal portion 371 extends from the end portion at the opposite side of the needle tip of the puncture needle 31 toward the perpendicular direction with respect to the plane including the arc of the puncture member 3 (with respect to the plane on which the puncture member 3 moves rotationally) (with respect to the orbital plane of the arc). The proximal portion 373 extends from the proximal portion of the distal portion 371 in the perpendicular direction toward the axial portion 33. More specifically, the proximal portion 373 extends from the proximal portion of the distal portion 371 in a direction perpendicular to the axial portion 33. The axial portion 33 extends perpendicularly from the center of the arc of the puncture needle 31 with respect to the plane including the arc of the puncture member 3.

It is also possible for the puncture apparatus 10''' shown in FIG. 26 to use one of the urethral-insertion member and the vaginal insertion member if it is possible to carry out the puncture by avoiding the urethra 100 and the vagina 200 carefully by specifying the positions of the urethra 100 and the vagina 200, for example, by monitoring with X-ray, ultrasound or the like. In this case, it is possible for the puncture apparatus 10''' shown in FIG. 26 to be formed to have constituent elements of a puncture needle 31 which is placed freely rotatably, which includes a bent region and which punctures living body tissue; an axial portion 33 which extends from the end portion at the opposite side of the needle tip of the puncture needle 31 through the L-shaped interlock portion 37; and a supporting portion 71 by which the axial portion 33 is placed freely rotatably.

In the configuration shown in FIG. 27, the interlock portion 37 forms an L-shape, but the shape of the interlock portion 37 is not so limited, and it is possible to employ a configuration which is formed, for example, by a linear shape, a curved shape, a shape made by combining a linear shape and a curved shape, or the like in which the portion is connected to the axial portion 33 so as not to interfere with the region of the rising portion of the aforesaid patient.

Also, in the present invention, it is possible, for example, to employ a configuration in which the vaginal-insertion member is omitted and the restriction means is provided so as to restrict only the positional relation between the puncture needle (puncture member) and the urethral-insertion member.

In the embodiments of the puncture apparatus described above, the orbit or path of movement of the puncture member is specified according to the positional relation with respect to the urethral-insertion member. But it is also possible to specify the orbit or path of movement according to the positional relation with respect to the vaginal insertion member. For example, it is possible to employ a configuration in which the orbit or path of movement of the puncture member passes a position which is on the position side near from the center point of the orbit and which is spaced from the vaginal insertion member by a predetermined distance. Thus, for example, with respect to a patient whose distance between the mid-urethra and the vagina was measured beforehand, it is possible for the orbit or movement path of the puncture member to pass a position which is on the position side near from the center point of the orbit and which is spaced from the vaginal insertion member by a distance shorter than the distance between the mid-urethra and the vagina.

The description above describes various embodiments in which the puncture apparatus is used in an apparatus that buries or positions a buriable implant for treatment of the woman's urinary incontinence into the inside of the living body. But the use of the puncture apparatus is not limited in this regard.

For example, the target to be applied with the puncture apparatus discloses here includes an excretory disorder along with the weakening of the pelvic floor muscle group (urinary urgency, frequent urination, urinary incontinence, fecal incontinence, urinary retention, dysuria or the like), and a pelvic floor disorder including pelvic organ prolapse, vesicovaginal fistula, urethrovaginal fistula, pelvic pain or the like. In the pelvic organ prolapse, there are include disorders of cystocele, enterocele, rectocele, hysterocele and the like. Alternatively, there are included disorders of anterior vaginal prolapse, posterior vaginal prolapse, vaginal vault prolapse, vaginal apical prolapse and the like in which the naming method thereof is based on the manipulating vaginal-wall regions.

Also, in the overactive tissues, there are included bladder, vagina, uterus, bowel and the like. In the lessactive tissues, there are included bones, muscles, fascias, ligaments and the like. In particularly, in the pelvic floor disorders, there are included an obturator fascia, a coccygeus fascia, a cardinal ligament, a uterosacral ligament, a sacrotuberous ligament and the like.

For the procedure for interlocking an overactive tissue in the pelvic floor disorder with the lessactive tissue, there are included a retropubic sling surgery, a transobturator sling surgery (Transobturator Sling surgery, Transobturator Tape: TOT), a tension-free vaginal mesh (Tension-free Vaginal Mesh: TVM) surgery, a uterosacral ligament suspension (Uterosacral Ligament Suspension: USLS) surgery, a sacrospinous ligament fixation (Sacrospinous Ligament Fixation: SSLF) surgery, an iliococcygeus fascia fixation surgery, a coccygeus fascia fixation surgery, and the like.

It is possible for the puncture apparatus disclosed here to be applied to the pelvic floor disorder as follows. It is possible for the puncture apparatus used for the pelvic floor disorder to be applied with the respective constructions of the puncture apparatuses of the above-described embodiments for treating urinary incontinence. As one embodiment, there are provided with a puncture member which is freely rotatably mounted, which includes a bent region and which includes a puncture needle for puncturing living body tissue; an insertion member having a longitudinal shape, which is to be inserted into the inside of the body; and a restriction structure for restricting the positional relation between the puncture member and the insertion member such that the needle tip of the puncture needle will pass at a far-position side from the rotation center of the puncture needle compared with the insertion member when the puncture member rotates and punctures the living body tissue.

For example, in the case of a rectocele, within the pelvic organ prolapses included in the pelvic floor disorders, in which the deviation occurs by the fact that the rectum pushes the vaginal wall, the overactive tissues are the rectum and the vagina and the lessactive tissue becomes the interlock region, or a muscle, a tendon or a ligament in the vicinity thereof.

As an example, one embodiment of a procedure for forming a path for burying an implant for treating the rectocele is as follows. First, a puncture apparatus is prepared and provided with a puncture member which is freely rotatably positioned, and which includes a bent region and which includes a puncture needle for puncturing living body tissue; an insertion member having a longitudinal (elongated) shape, which is to be inserted into the inside of the living body; and a restriction structure for restricting the positional relation between the puncture member and the insertion member such that the needle tip of the puncture needle will pass a far-position side (be spaced from) from the rotation center of the puncture needle compared with the insertion member when the puncture member rotates and punctures the living body tissue. Next, the insertion member is inserted into a rectum of a patient. Further, the puncture needle of the puncture member is operated to puncture a body surface at one buttock region of the patient or at the region in the vicinity thereof, made to enter into the body, made to pass a far-position side of the rectum, made to protrude to the outside of the body from the body surface of another buttock region or from the region in the vicinity of such region, whereby there is formed a through-hole reaching the far-position side of the rectum and the another buttock region or the region in the vicinity of such region from the other buttock region or the region in the vicinity of such region. After forming the through-hole, a mesh-shaped implant is indwelled by an identical or similar method as that of the urinary incontinence described above.

For another embodiment of the procedure disclosed by way of example, there is a method in which there is prepared a puncture member which is freely rotatable, which includes a bent region and which includes a puncture needle for puncturing living body tissue; and when the puncture member is moved rotationally and the puncture needle of the puncture member punctures the living body tissue, the puncture needle is made to puncture a body surface at a buttock region of the patient or at the region in the vicinity thereof and is made to enter into the body; and the puncture member is made to pass a far-position side from the rotation center of the puncture needle compared with a rectum which is the target region, whereby the path is formed.

An another embodiment of the procedure, there is prepared a puncture tool provided with an insertion member having a longitudinal (elongated) shape, which is to be inserted into the inside of a rectum, and a puncture member which can puncture the living body tissue and which has such an orbit or movement path passing a far-position side compared with the insertion member; the insertion member is inserted into the rectum of a patient; the puncture member is made to puncture into the body surface at a buttock region of the patient or at the region in the vicinity of such region; and the puncture member is made to pass a far-position side compared with the insertion member, whereby the path is formed. The insertion member is not limited to a member which is inserted into a tubular lumen having an opening on the surface of the living body, such as a vagina, a urethra, a rectum and the like, and there can be included also a configuration in which the insertion member punctures the tissue from the surface of the living body. In case of puncturing the tissue from the surface of the living body, it is preferable for a tissue insertion member to be provided with a marker by which the position of the tissue insertion member can be confirmed or identified. By providing a marker, there can be confirmed the position at which the insertion member punctures the tissue. For the marker, it is possible to attach a visually-recognizable marker by which the insertion depth is visually recognizable. Also, for the marker, it is preferable to use a marker which is visually recognizable under a noninvasive monitoring inside the body.

The target to be applied is not limited by the pelvic floor disorder. For example, the apparatus and method are also applicable to a disorder in which position deviation of an organ occurs in the inside of the living body such as a case of an interlock hernia, an abdominal wall hernia or the like.

A puncture apparatus disclosed here generally includes a freely rotatable puncture member which includes a bent region and which includes a puncture needle for puncturing living body tissue, a urethral-insertion member having an elongated shape which is to insertable into the inside of a urethra, and restriction means for restricting the positional relation between the puncture member and the urethral-insertion member such that the needle tip of the puncture needle will pass a far-position side from the rotation center of the puncture needle compared with the urethral-insertion member when the puncture member rotates and punctures the living body tissue.

When burying an implant for example, burden onto a patient is relatively small, safety of the patient is quite good and also the safety of the operator is rather high.

When using the puncture apparatus for treating a woman's urinary incontinence, for example, the urethral-insertion member of aforesaid puncture apparatus is inserted into her urethra, the puncture needle is moved rotationally, and her living body is punctured by the puncture needle. At that time, the needle tip of the puncture needle passes a far-position side from the center of the puncture needle compared with the urethral-insertion member, so that it is possible to puncture the living body by avoiding the urethra and it is possible to prevent a phenomenon that the puncture needle is to puncture the urethra. Also, it is possible to prevent a phenomenon that the finger tip of the operator is punctured by the puncture needle.

Also, when burying an implant for treatment of the urinary incontinence, incision of a vagina wall is not necessary and it is possible to bury that implant by a relatively low invasive procedure. Also, it is possible to prevent a phenomenon in which, such as in a case of incising a vagina, the implant will be exposed to the inside of the vagina from a wound caused by the incision and in which there occur complications which are to be caused by an infection from the wound or the like, and it is very safe and it is possible to bury the implant reliably.

Also, similar benefits can be realized for disorders in which a position deviation of an organ occurs in the inside of the living body such as a case of a pelvic floor disorder or the like.

The puncture apparatus and method here thus exhibit industrial usability.

Having described, by way of example, embodiments of the puncture apparatus and method, it is to be understood that the invention here is not limited to those precise embodiments and that various changes and modifications could be effected therein by one skilled in the art without departing from the spirit or scope of the invention as defined in the claims.

What is claimed is:

1. A puncture apparatus comprising:
   a freely rotatable puncture member possessing a distal end portion and a proximal end portion, the puncture member including a bent region at which the puncture member is bent, the distal end portion of the puncture member including a puncture needle for puncturing living body tissue as the puncture member is rotated about a rotation center to rotate a needle tip of the puncture needle toward the living body tissue to puncture the living body tissue;
   an elongated urethral-insertion member configured to be inserted into a urethra so that a near-side of the urethral-insertion member is the side of the urethral-insertion member located closer to the rotation center, and the far-side of the urethral-insertion member is the side of the urethral-insertion member located farther from the rotation center; and
   restriction means for restricting a positional relationship between the puncture member and the urethral-insertion member so that the needle tip of the puncture needle which is rotating about the rotation center after first puncturing the living body tissue passes on the far-side of the urethral-insertion member.

2. The puncture apparatus according to claim 1, further comprising an elongated vaginal-insertion member sized and configured to be inserted into a vagina, the restriction means also restricting the positional relationship between the puncture member and the vaginal-insertion member such that the needle tip of the puncture needle will not intersect the vaginal-insertion member when the puncture member is rotating about the rotation center after first puncturing the living body tissue.

3. The puncture apparatus according to claim 1, wherein the puncture member includes an axial portion possessing a central axis which is also a rotational axis for rotational movement of the puncture member, and the restriction means supports the axial portion in a freely rotatable manner, the restriction means also including a supporting member supporting the urethral-insertion member.

4. The puncture apparatus according to claim 3, wherein the puncture member is freely detachably mounted on the supporting member.

5. The puncture apparatus according to claim 3, wherein the axial portion is supported by the supporting member movably in the axial direction of the urethral-insertion member.

6. The puncture apparatus according to claim 1, further comprising an elongated vaginal-insertion member sized and configured to be inserted into a vagina, the puncture member including an axial portion possessing a central axis which is also a rotational axis for rotational movement of the puncture member, wherein the restriction means restricts the positional relationship between the puncture member and the vaginal-insertion member such that the needle tip of the puncture needle will not intersect the vaginal-insertion member when the puncture member is rotating about the rotation center after first puncturing the living body tissue, and the restriction means supporting the axial portion in a freely rotatable manner and concurrently, the restriction means also including a supporting member supporting the urethral-insertion member and the vaginal-insertion member respectively.

7. The puncture apparatus according to claim 1, wherein the puncture member includes an axial portion connected to the puncture needle, the axial portion and the urethral-insertion member each possessing a respective axis, the axis of the axial portion being inclined with respect to the axis of the urethral-insertion member such that a distance of separation between the axis of the axial portion and the axis of the urethral-insertion member increases or decreases is a distal direction.

8. The puncture apparatus according to claim 1, wherein the puncture member includes an operation unit operatively connected to the puncture member so that operation of the operation member rotates the puncture member.

9. The puncture apparatus according to claim 1, wherein the puncture needle possesses a distal end portion provided with a through-hole.

10. The puncture apparatus according to claim 1, wherein the urethral insertion portion possesses a tubular shape.

11. The puncture apparatus according to claim 1, further comprising a guide member for guiding the puncture needle.

12. A puncture apparatus comprising:
a freely rotatable puncture member possessing a distal end portion and a proximal end portion, the puncture member including a bent region at which the puncture member is bent, the distal end portion of the puncture member including a puncture needle for puncturing living body tissue as the puncture member is rotated about a rotation center to rotate a needle tip of the puncture needle toward the living body tissue to puncture the living body tissue;
an elongated insertion member configured to be inserted inside a living body so that a near-side of the insertion member is the side of the insertion member located closer to the rotation center, and the far-side of the insertion member is the side of the insertion member located farther from the rotation center; and
a restriction structure which restricts a positional relationship between the puncture member and the insertion member to position the needle tip of the puncture needle which is rotating about the rotation center after first puncturing the living body tissue on the far-side of the insertion member.

13. The puncture apparatus according to claim 12, wherein the insertion member is a tubular-lumen insertion member sized and configured to be inserted into a tubular lumen opened in the living body.

14. The puncture apparatus according to claim 12, wherein the insertion member is a tissue-insertion member sized and configured to puncture a surface of the living body.

15. The puncture apparatus according to claim 14, wherein the insertion member includes either a depth marker by which an insertion depth of the insertion member is visually recognizable or a depth marker by which the insertion depth of the insertion member is visually recognizable under a noninvasive monitoring inside the living body.

16. The puncture apparatus according to claim 12, wherein the restriction structure comprises a supporting member, the puncture member being positioned in a through hole in the supporting member so that both the proximal end portion and the distal end portion of the puncture member are positioned outside the supporting member, with the bent portion positioned outside the supporting member on a distal side of the supporting member, the insertion member being fixed to the supporting member and extending in a distal direction away from the supporting member.

17. The puncture apparatus according to claim 12, wherein the restriction structure comprises a supporting member, the supporting member including a first supporting portion and a second supporting portion which are connected to one another, the insertion member being fixed to the first supporting portion and extending in a distal direction away from the first supporting portion, the puncture member being freely rotatably mounted on the second supporting portion and supported either in an arc-shaped groove permitting the puncture member to rotate about the rotation center or on an arc-shaped surface permitting the puncture member to rotate about the rotation center.

18. A method of forming a path in living body tissue comprising:
inserting an elongated insertion member of a puncture apparatus into a portion of a living body, the puncture apparatus also including a rotatable puncture member possessing a distal end portion at which is located a needle tip;
rotating the puncture member in a rotational direction about a rotation center while the insertion member remains inserted in the living body to move the puncture member along a path of rotational movement, the portion of the living body into which the insertion member is inserted being located relative to the rotation center of the path of rotational movement of the puncture member such that a near-side of the insertion member is the side of the insertion member located closer to the rotation center, and a far-side of the insertion member is the side of the insertion member located farther from the rotation center;
continuing to rotate the puncture member in the rotational direction about the rotation center while the insertion member remains inserted in the living body to cause the needle tip to puncture a surface of the living body tissue; and restricting a positional relationship of the puncture member and the insertion member while rotating the puncture member in the rotational direction to ensure that the path of rotational movement of the puncture member passes on the far-side of the insertion member.

19. The method according to claim 18, wherein the needle tip punctures the surface of the living body tissue at a first location, the method further comprising continuing to rotate the puncture member in the rotational direction until the needle tip penetrates the surface of the living body tissue to exit the living body tissue at a second location spaced from the first location.

20. The method according to claim 19, further comprising fixing one end of an implant to the needle tip after the needle tip exits the living body tissue at the second location.

* * * * *